US009738891B2

(12) United States Patent
Leumann et al.

(10) Patent No.: US 9,738,891 B2
(45) Date of Patent: Aug. 22, 2017

(54) TRICYCLO-PHOSPHOROTHIOATE DNA

(71) Applicants: ASSOCIATION INSTITUT DE MYOLOGIE, Paris (FR); UNIVERSITAT BERN, Bern (CH); UNIVERSITE PIERRE ET MARIE CURIE (PARIS 6), Paris (FR); INSTITUT NATIONAL DE LA SANTE ET DE LA RECHERCHE MEDICALE, Paris (FR); CENTRE NATIONAL DE LA RECHERCHE SCIENTIFIQUE, Paris (FR)

(72) Inventors: Christian Leumann, Bern (CH); Luis Garcia, impasse de l'Etang (FR); Thomas Voit, Boullay les Troux (FR)

(73) Assignees: ASSOCIATION INSTITUT DE MYOLOGIE, Paris (FR); UNIVERSITAT BER, Bern (CH); CENTRE NATIONAL DE LA RECHERCHE SCIENTIFIQUE, Paris (FR); INSTITUT NATIONAL DE LA SANTE ET DE LA RECHERCHE MEDICALE, Paris (FR); UNIVERSITE PIERRE ET MARIE CURIE (PARIS 6), Paris (FR)

( * ) Notice: Subject to any disclaimer, the term of this patent is extended or adjusted under 35 U.S.C. 154(b) by 0 days.

(21) Appl. No.: 14/351,733

(22) PCT Filed: Oct. 12, 2012

(86) PCT No.: PCT/EP2012/070349
§ 371 (c)(1),
(2) Date: Apr. 14, 2014

(87) PCT Pub. No.: WO2013/053928
PCT Pub. Date: Apr. 18, 2013

(65) Prior Publication Data
US 2014/0296323 A1    Oct. 2, 2014

Related U.S. Application Data

(60) Provisional application No. 61/546,942, filed on Oct. 13, 2011.

(30) Foreign Application Priority Data

Oct. 13, 2011  (EP) .................................... 11185129
Apr. 27, 2012  (CA) .................................... 2776651

(51) Int. Cl.
 $C07H\ 21/04$ (2006.01)
 $C12N\ 15/113$ (2010.01)
 $C12N\ 15/11$ (2006.01)

(52) U.S. Cl.
CPC .......... $C12N\ 15/113$ (2013.01); $C12N\ 15/111$ (2013.01); $C12N\ 2310/11$ (2013.01); $C12N\ 2310/315$ (2013.01); $C12N\ 2310/3231$ (2013.01); $C12N\ 2320/33$ (2013.01)

(58) Field of Classification Search
CPC ...................................................... C07H 21/04
See application file for complete search history.

(56) References Cited

U.S. PATENT DOCUMENTS

2010/0016215 A1*  1/2010  Moulton ................ C12N 15/87
                                                    514/1.1

FOREIGN PATENT DOCUMENTS

WO           2004/092191 A2     10/2004
WO        WO 2010/115993        10/2010
WO        WO 2012/115993         8/2012

OTHER PUBLICATIONS

International Search Report for International Application No. PCT/EP2012/070349 mailed Nov. 30, 2012 (3 pages).
Kaplan. "Vers des essais cliniques de therapies geniques et cellulaires combines au sait d'exon poor la myopathie de Duchenne." *BILAN ICE-2010*. 2011. http//www.duchennefr.com/medias/ice-2010-bilan.pdf.
Ittig et al. "Position-dependent effects on stability in tricycle-DNA modified oligonucleotide duplexes." *Nucleic Acids Research*. vol. 39. No. 1. 2011. pp. 373-380.
Ivanova et al. "Tricyclo-DNA Containing Oligonucleotides as Steric Block Inhibitors of Human Immunodeficiency Virus Type 1 Tat-Dependent Trans-Activation and HIV-1 Infectivity." *Oligonucleotides*. vol. 17. 2007. pp. 54-65.
Murray et al. "TricycloDNA-modified oligo-2'-deoxyribonucleotides reduce scavenger receptor B1 mRNA in hepatic and extra-heptatic tissues—a comparative study of oligonucleotide length, design and chemistry." *Nucleic Acides Research*. vol. 40. No. 13. 2012. pp. 6135-6143.

* cited by examiner

*Primary Examiner* — Kimberly Chong
(74) *Attorney, Agent, or Firm* — Arrigo, Lee & Guttman LLP

(57) ABSTRACT

The present invention relates to a nucleic acid molecule containing a sequence of tricyclo nucleosides joined by internucleoside phosphorothioate linkage. The invention also relates to synthetic antisense oligonucleotides and to methods employing the same.

8 Claims, 19 Drawing Sheets

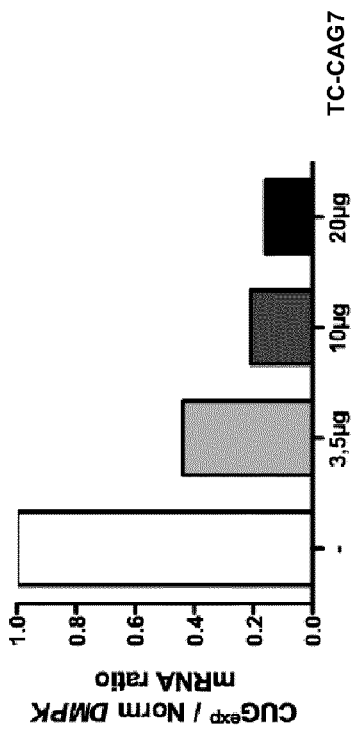
Figure 16
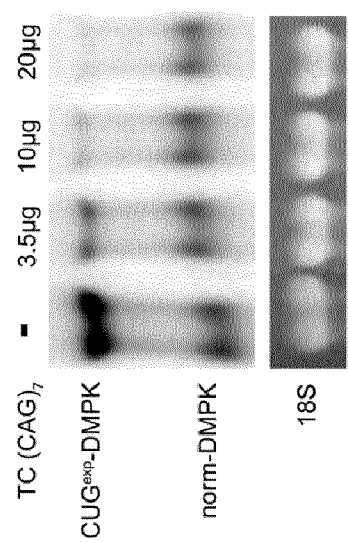

US 9,738,891 B2

TRICYCLO-PHOSPHOROTHIOATE DNA

FIELD OF THE INVENTION

The present invention relates to a nucleic acid molecule containing a sequence of tricyclo nucleosides joined by internucleoside phosphorothioate linkages. The invention also relates to synthetic antisense oligonucleotides and to methods employing the same.

BACKGROUND OF THE INVENTION

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs.

Recently, the present inventors have proposed to use the advantageous properties of this class of nucleic acids in antisense oligonucleotides for the treatment of a number of diseases. International application No. PCT/EP2010/054735 discloses synthetic antisense oligonucleotides and methods employing antisense oligonucleotides for modifying splicing events that occur during pre-mRNA processing or for down-regulating the expression of mutated mRNA that contain repeated sequences such as, for example, 3' or 5' CUG, CAG, and/or CCUG. More specifically, it was shown that tricyclo-DNA antisense oligonucleotides are effective in facilitating exon skipping during pre-mRNA processing, in masking intronic silencer sequences and/or stem-loop sequences in pre-mRNA, and in targeting the RNase-mediated destruction of mRNA.

Duchenne Muscular Dystrophy (DMD) is the most common hereditary myopathy, afflicting about one in 3,500 males regardless of ethnicity. The foremost consequence of DMD is that muscle fibers become particularly fragile and natural muscle activity provokes general damage in muscle tissue. Lack of dystrophin makes that muscle fibers are particularly vulnerable to mechanical stress, and undergo recurrent cycles of necrosis. As a result, patients display progressive weakness of skeletal muscles, which are with time replaced by adipofibrotic tissue, leading to loss of ambulation around the age of twelve, whereupon premature death is caused by either respiratory failure or cardiomyopathy between the second and fourth decade. In addition, about one third of DMD patients also display cognitive impairment suggesting a noteworthy disruption of neuronal and brain function. DMD affects all voluntary muscles and involves the heart and breathing muscles in later stages of the disease. Heart and CNS should thus preferably be targeted by any therapy implemented to treat or alleviate the symptoms of DMD patients.

A new class of compounds was sought that have improved efficiency when compared to tricyclo-DNA oligonucleotides. The present invention describes the synthesis, properties and uses of tricyclo-phosphorothioate nucleotides.

SUMMARY OF THE INVENTION

The present inventors have surprisingly shown that nucleic acid molecules comprising tricyclo-phosphorothioate nucleotides are, in addition to their ability shared with tc-DNA molecules to be active in a wide range of muscles, highly efficient in penetrating cardiac tissue and are highly active in cardiac cells. It has also been shown that such tricyclo-phosphorothioate nucleotides are capable of rescuing the expression of a protein, in particular dystrophin, in CNS after systemic delivery. The inventors have therefore shown the unexpected property of nucleic acid molecules comprising tricyclo-phosphorothioate nucleotides to cross the blood-brain barrier.

The invention thus relates to nucleic acid molecules comprising tricyclo-nucleosides joined by internucleoside phosphorothioate linkages (3'-OPS—O-5' linkages). The nucleic acid molecules of the invention are also referred to as "tricyclo-phosphorothioate DNA" or "tc-DNA-PS" in the present disclosure.

The invention also relates to a composition comprising a tc-DNA-PS and a carrier. The composition can in particular be a pharmaceutical composition, wherein the carrier is a pharmaceutically acceptable carrier. The composition of the invention can also optionally comprise an additional active agent.

The present invention also relates to a method for synthesizing tc-DNA-PS molecules.

The inventive nucleic acid molecules are particularly useful as antisense oligonucleotides (AONs), in particular for obtaining an antisense effect in muscles and in cardiac cells, or in the CNS, in particular after systemic delivery of the AON. The present invention thus also provides tc-DNA-PS AONs Since the inventors have shown that after systemic delivery, a tc-DNA-PS AON according to the invention can correct the expression of dystrophin in muscles, in the cardiac tissue and in the CNS, the invention further relates to methods employing tc-DNA-PS AONs for the treatment of diseases. Representative diseases include for example heart diseases such as hypertrophic obstructive cardiomyopathy caused by cMYBP-C mutations and neuromuscular diseases such as Duchenne Muscular Dystrophy, Spinal Muscular Atrophy, and Steinert's Myotonic Dystrophy. More generally, the invention relates to a method of correcting abnormal gene expression in a cell of a subject, the method comprising administering to the subject a tc-DNA-PS antisense oligonucleotide, wherein said tc-DNA-PS antisense oligonucleotide is complementary to a portion of an RNA encoded by said gene. In a preferred embodiment, the said tc-DNA-PS antisense oligonucleotide is administered peripherally to the subject in an amount sufficient to correct said abnormal expression. Preferred peripheral administration includes systemic injection such as intravenous, subcutaneous, intraperitoneal or intra-arterial injection.

The invention also relates to a method of treating a genetic disease caused by abnormal gene expression in a tissue or cell of a subject, the method comprising administering to the subject a tc-DNA-PS antisense oligonucleotide, wherein said tc-DNA-PS antisense oligonucleotide is complementary to a portion of an RNA encoded by said gene. The tc-DNA-PS antisense oligonucleotide is preferentially administered peripherally to the subject in an amount sufficient to correct said abnormal expression. In particular, the tissue or cell can be selected from muscle, cardiac and CNS tissues or cells.

Tc-DNA-PS in the present invention are shown to be transported in the blood stream after subcutaneous or intravenous/intraperitoneal systemic application to all skeletal muscles, to the CNS and to cardiac muscle and to be taken up by these tissues.

Other objects and applications will become apparent from the following detailed description of the invention.

(A) Effects of M23D tc-DNA-PS in the CNS after systemic delivery (Dose: 200 and 50 mg/kg/week; Route: intravenous; Duration: 12 weeks). RNA samples from either whole brain or cerebellum were analyzed by nested RT-PCR using specific primers specifically amplifying the exon 23 skipped dystrophin mRNA (398 bp amplicon). A sample from the tibialis anterior of a treated mdx was used as positive control. (B) Percentage of exon skipping analyzed by Taqman qPCR in the whole brain and the cerebellum of treated animals (n=3 per group).

Figure 9:
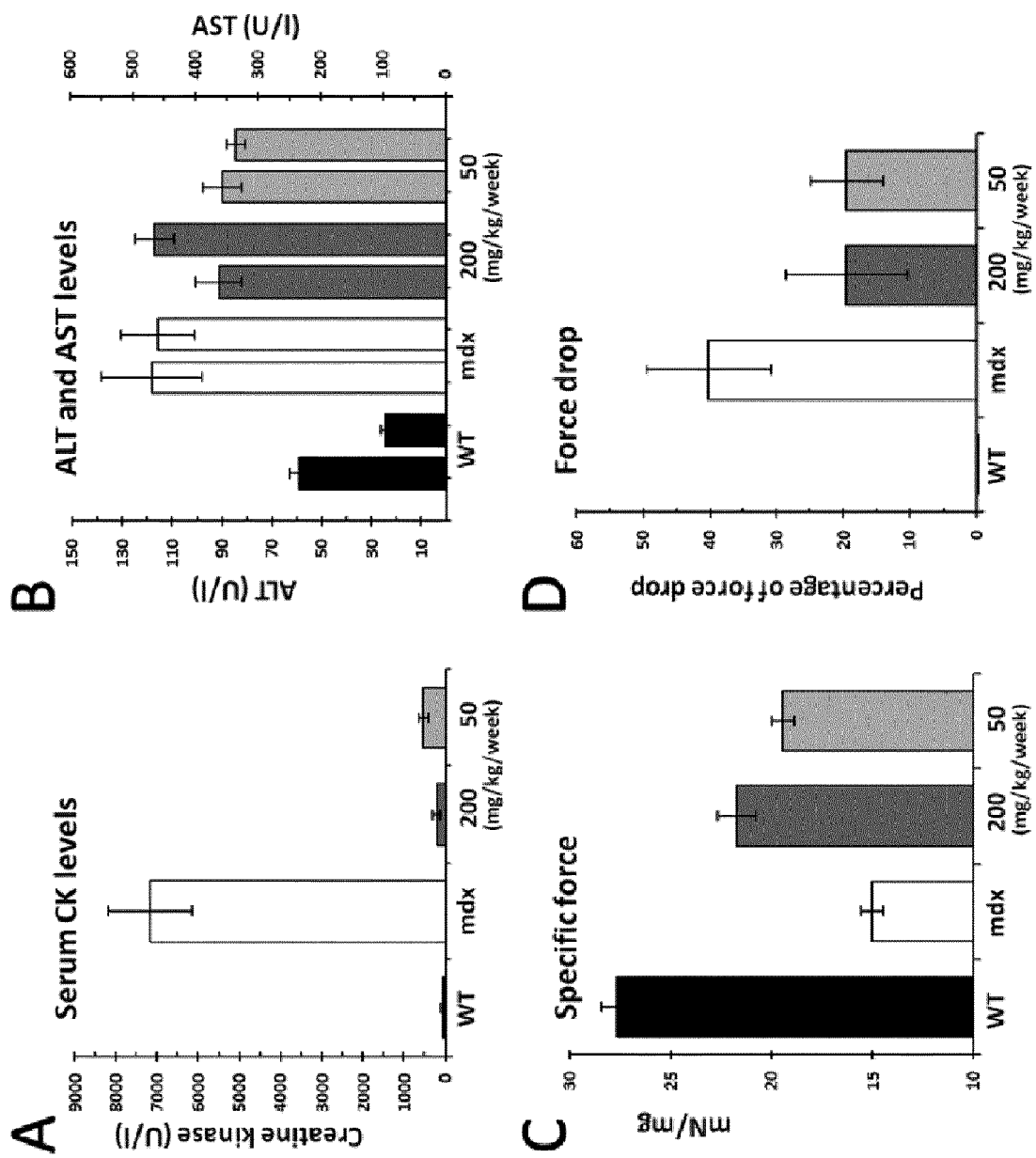

FIG. 9 presents experiments showing that systemic delivery of tc-DNA-PS (M23D+2-13) improved the mdx phenotype. (A) Serum creatine kinase levels in treated animals compared to wild type and untreated mdx (n=3 per group). P<0.001 for 200 mg/kg/wk and p<0.05 for 50 mg/kg/wk. (B) For both regimens (200 or 50 mg/kg), ALT and AST levels in serum advocate that tc-DNA-PS did not elicit hepatic toxicity. P>0.05 compared to untreated mdx mice. (C) Improvement of muscle function in tc-DNA-PS treated mice. Tibialis anterior (TA) muscles of treated mdx mice were analyzed for their specific force (maximal force normalized for cross-sectional area). p<0.001 for 200 mg/kg/wk and p<0.05 compared to untreated mice. (D) The percentage of force drop was assessed by measuring the force deficit following a series of three eccentric contractions. Values confirm that muscles in treated mdx animals were more resilient than in untreated mdx. Force drop in treated mice (200 and 50 mg/kg/wk) is not significantly different from wild type.

Figure 10:
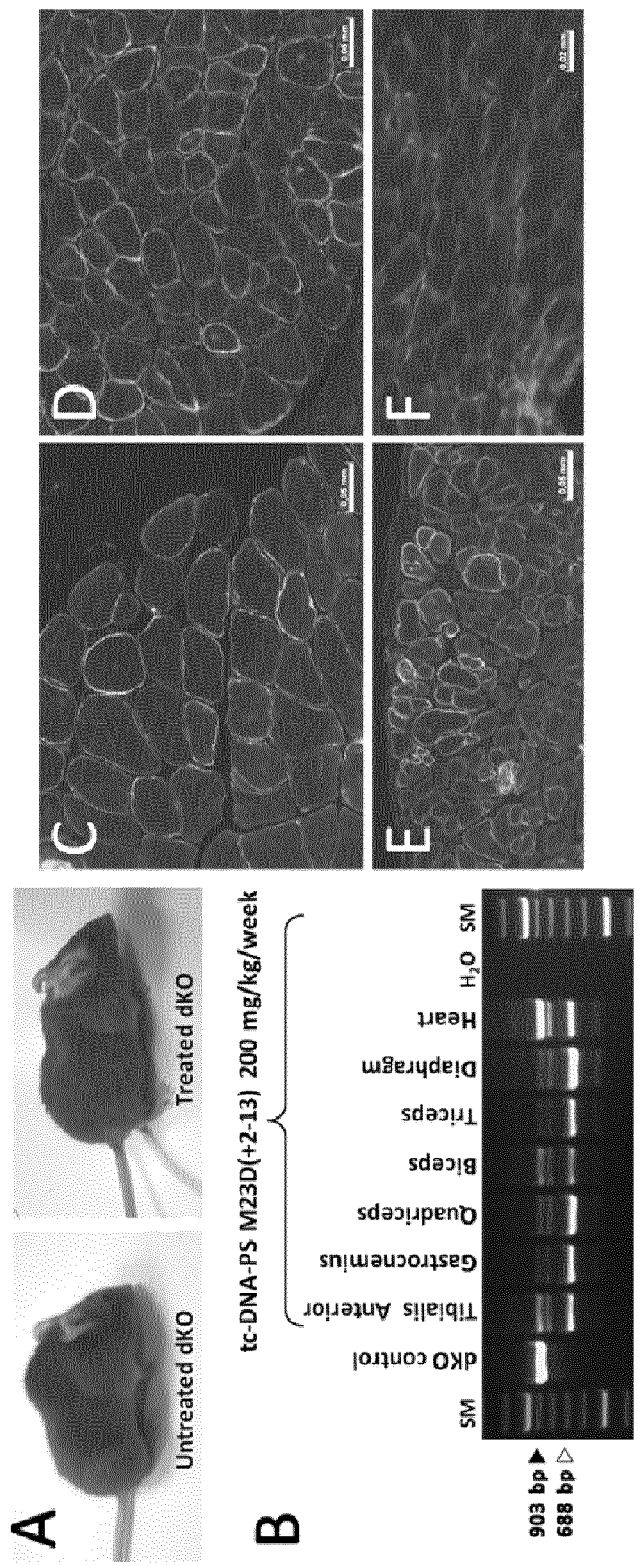
Figure 10:
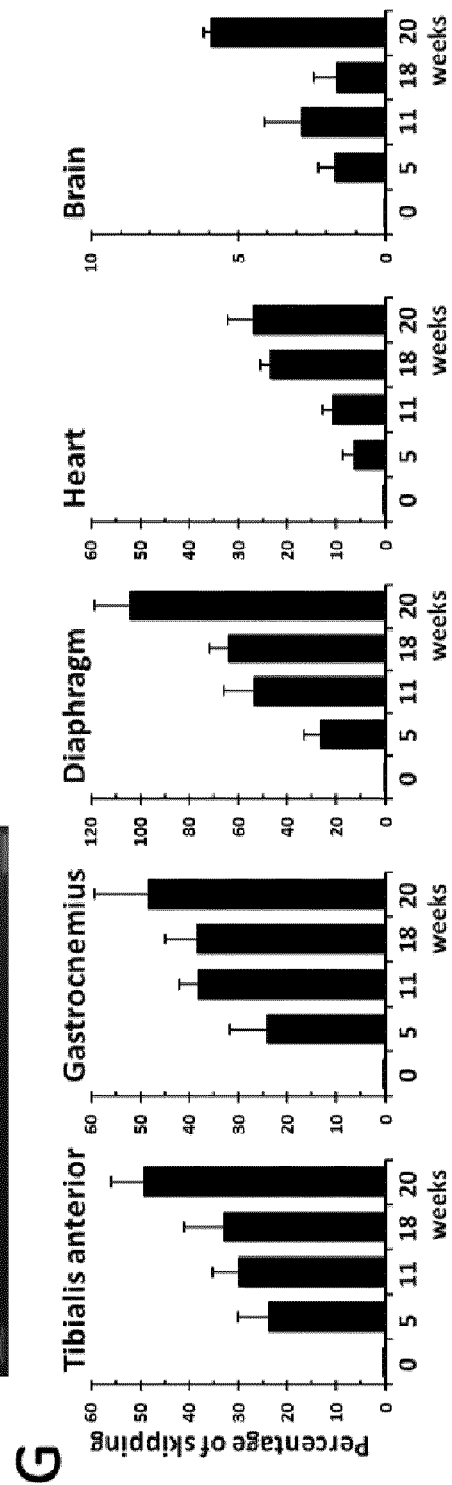

FIG. 10 presents experiments showing dystrophin rescue in the dKO mouse model after intravenous delivery of tc-DNA-PS (M23+2-13).

(A) Systemic treatment with tc-DNA-PS(M23D+2-13) (Dose: 200 mg/kg/week; Route: intravenous and subcutaneous alternating) averts the onset of dystrophic pathology in dKO mice. Photograph of an untreated dKO mouse at 12 weeks of age (left), displaying a strong kyphosis and joint contractures compared with a treated litter mate (right), looking healthy. Treatment was initiated at 3 weeks of age. (B) Detection of exon 23-skipped dystrophin mRNA in dKO muscles after systemic delivery tc-DNA-PS (Dose: 200 mg/kg/week; Route: intravenous and subcutaneous alternating; Duration: 20 weeks). RNA samples were analyzed at 2 weeks after the end of the treatment by nested RT-PCR as previously described. The 688-bp fragment that corresponds to the exon 23-skipped mRNA was detected in all tested muscles including heart. (C-F) Dystrophin immunostaining on transverse sections from muscles of treated dKO: (C) tibialis anterior; (D) gastrocnemius; (E) diaphragm; (F) heart. Sections from untreated animals were devoided of dystrophin staining Nuclei were counterstained with Dapi (blue). (G) Percentage of exon skipping analyzed by Taqman qPCR in different muscles and brain after 5, 11, 18 or 20 injections.

Figure 11:
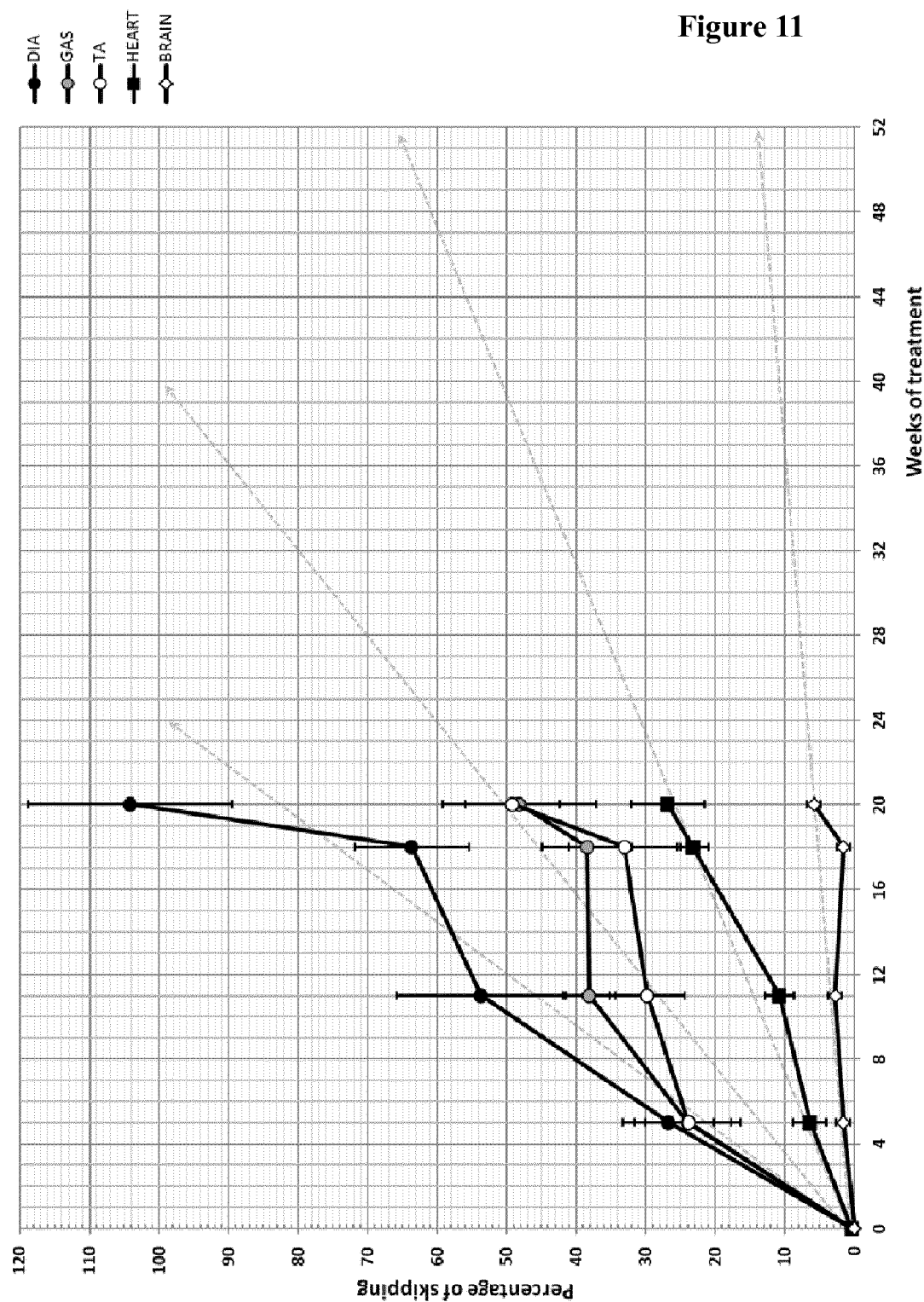

FIG. 11 is a diagram showing the expected outcomes after one year treatment. Accordingly to the cumulative effect of repeated systemic injections, it is expected that maximal effect of the treatment would be attained at about 20 weeks for the diaphragm (observed during the course of the experiment) and 40 weeks for other skeletal muscles. One could also expect that exon skipping would reach 60% in cardiac muscle and about 15% in CNS.

Figure 12:
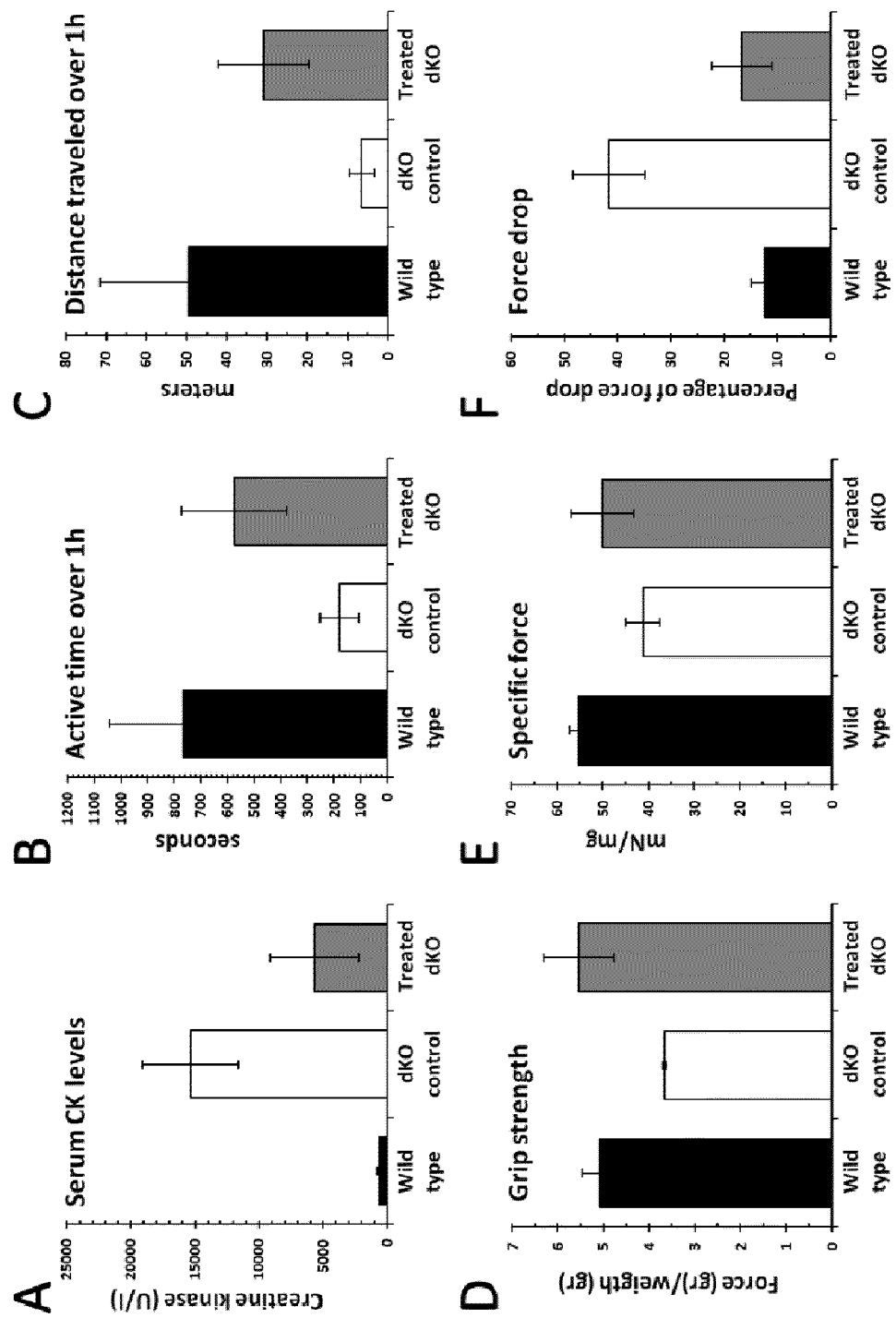

FIG. 12 presents experiments showing that systemic delivery of tc-DNA-PS (M23D+2-13) improved the dKO phenotype.

(A) Serum creatine kinase levels in treated animals compared to wild type and untreated dKO (n=5 per cohort) (p<0.05). (B and C) Mice were analyzed at 10 weeks of age with open-field behavioural activity cages. (B) cumulated active time and (C) distance travelled over 1 hour (n=5 per cohort). (D-F) Improvement of muscle function in tc-DNA-PS treated mice. (D) Forelimb muscle function assessment shows a physical improvement in treated dKO P<0.05. (E) Extensor digitorum longus (EDL) muscles of treated dKO mice were analyzed for their specific force (maximal force normalized for cross-sectional area). (F) The percentage of force drop is assessed by measuring the force deficit following a series of 5 eccentric contractions. p<0.05 compared to untreated dKO mice. Values confirm that muscles in treated dKO animals were more resilient than in untreated dKO. Error bars are shown as mean±SEM (N=5 per cohort).

Figure 13:
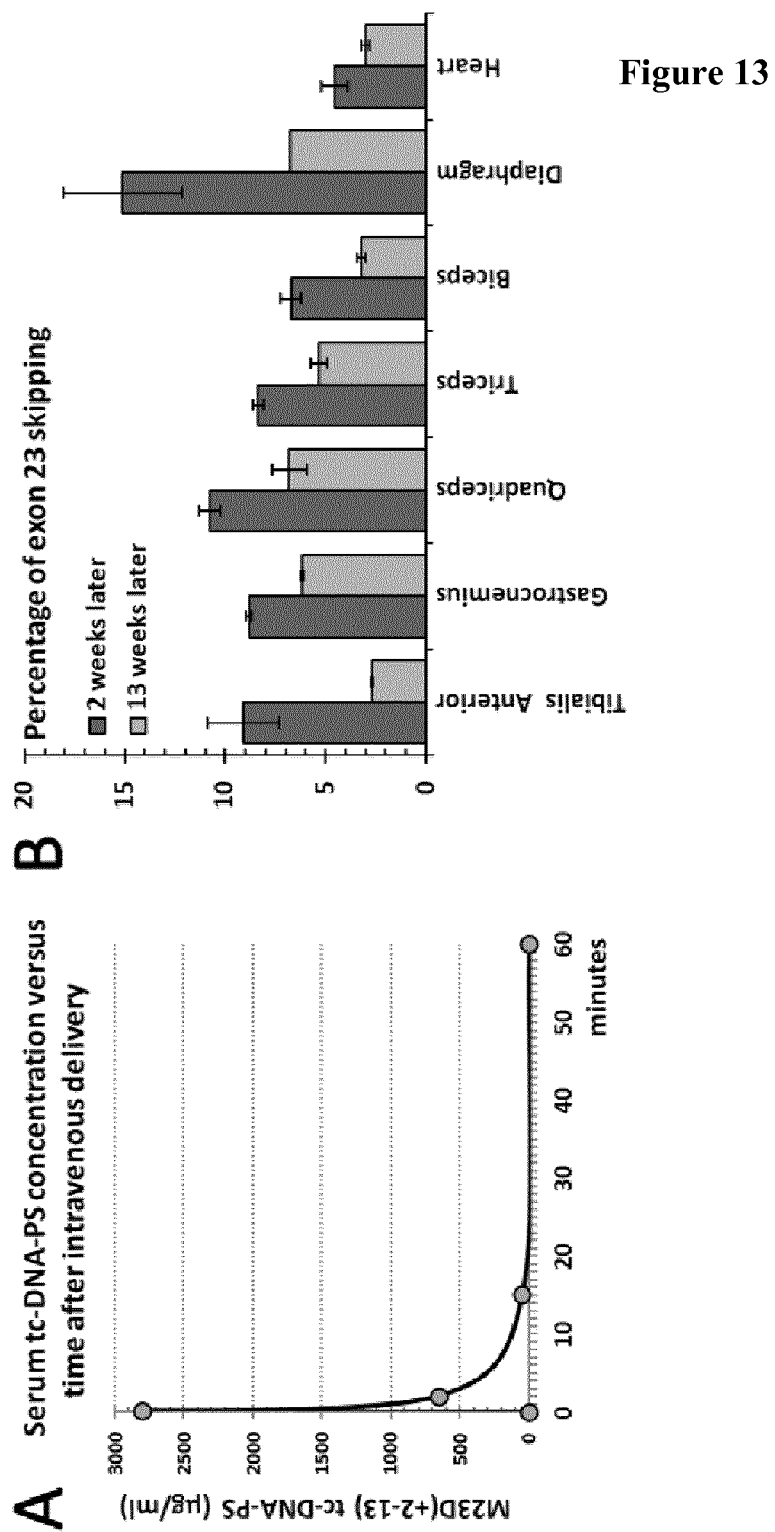
Figure 14:
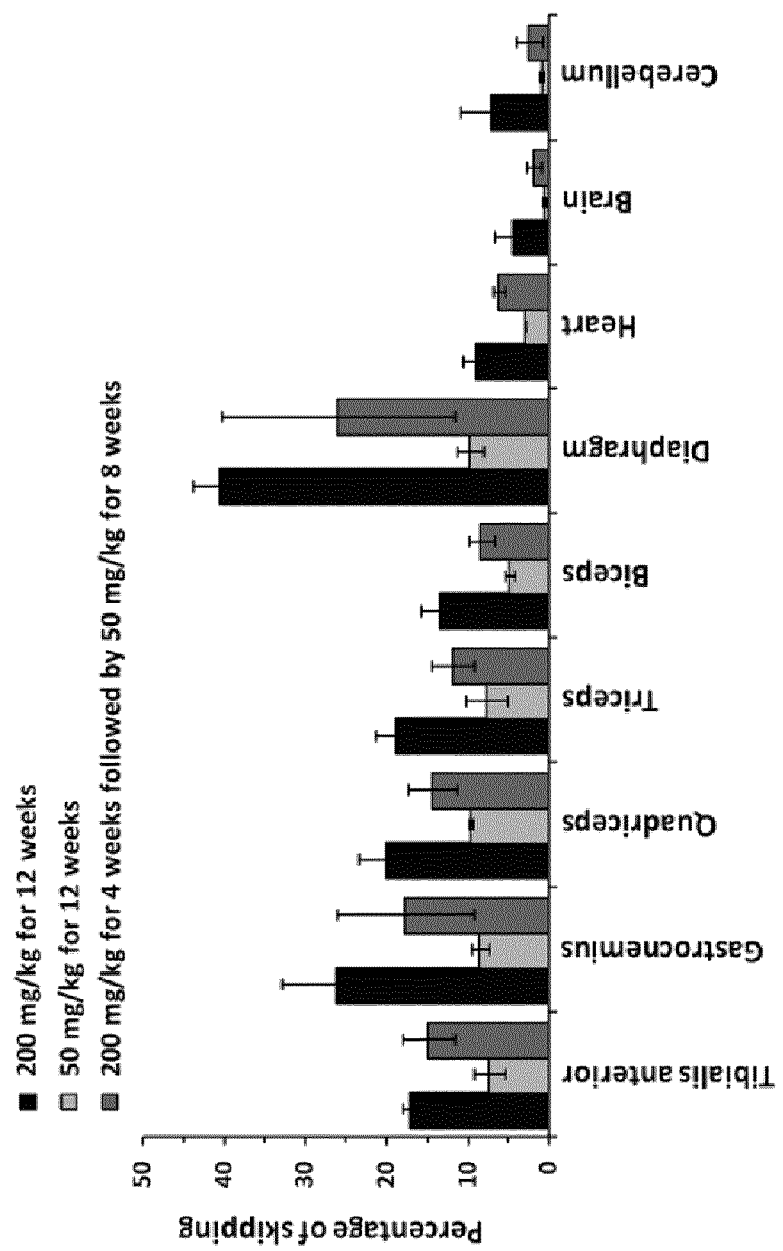

FIGS. 13 and 14 present experiments showing the lasting effect of tc-DNA-PS (M23D+2-13). FIG. 13 shows pharmacokinetic of tc-DNA-PS (M23D+3-13) after intravenous injection (A). Mice received a single injection of oligonucleotides at the concentration of 200 mg/kg. Serum samples were collected at different time points and analyzed by HPLC-MS/MS to appraise tc-DNA-PS levels in the blood compartment. (B) Durableness of the treatment was assessed by comparing the percentage of skipping in animals loaded with the same amount of tc-DNA-PS (total amount of about 15 mg) but analyzed at either 2 weeks or 13 weeks after the end of the treatment. Importantly, about 3 months after the last injection, levels of skipping were still significantly very high representing almost half of the initial outcome as measured at 2 weeks after treatment. This suggests that tc-DNA-PS are stable in cells and could be re-employed over time thus limiting the need to fill up tissues as often it would be required if these oligos were destroyed or tittered by their mRNA target.

FIG. 14 shows another way to test persistence of the effect of the treatment. Three sets of animals were treated with the same amount of tc-DNA-PS M23D(+2-13). Set 1 for 12 weeks at 200 mg/kg/week, Set 2 for 12 weeks at 50 mg/kg/week and Set 3 for 4 weeks at 200 mg/kg/week followed by 8 weeks at 50 mg/kg/week. Muscles were collected 2 weeks after the end of the treatment and analyzed by Taqman RT-qPCR. (n=3 per cohort).

Figure 15:
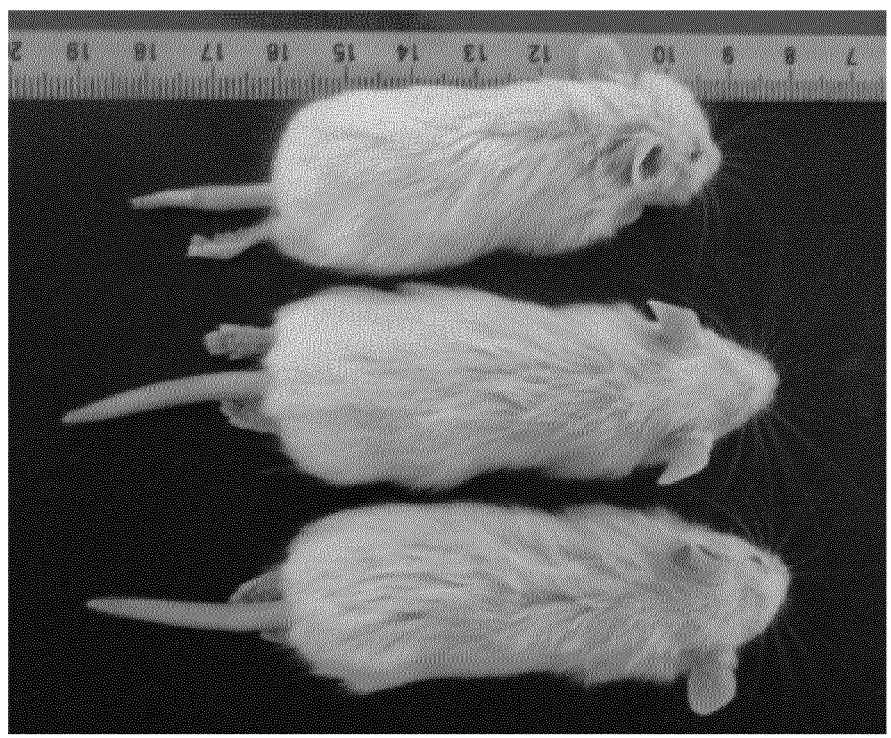

FIG. 15 shows the effect of systemic delivery of tc-DNA-PS (ISS7) in the SMA mouse model (FVB.Cg-Tg(SMN2) 2Hung Smn1tm1Hung/J).

SMA Type III mice (FVB.Cg-Tg(SMN2)2Hung Smn1$^{tm1Hung}$/J) are knock out for Smn (Smn1−/−) and contain a SMN2 transgene made of two tandem copies of the human SMN2 gene. These animals display typical features including necrosis of the tail starting at about one month of age. Such a necrosis progressively extends to the pinnae of the ears and feet and late in life these animals present with muscle weakness.

The photograph shows 3 type III individuals (one month old). The upper one is an untreated control showing typical necrosis of the tail; the two others, treated with tc-DNA-PS (ISS7) do not show such a feature indicating SMN2 gene are rescued by inclusion of the exon 7 thus giving rise to SMN: They received a single injection ICV (intracerebroventricular) at birth (5 µl containing 20 µg of tc-DNA-PS (ISS7)) and repeated SC (subcutaneous) injections once a week at a dose of 200 mg/kg.

FIG. 16 present an experiment showing the in vitro efficiency of a tc-DNA oligonucleotide targeting CUG amplifications.

Figure 17:
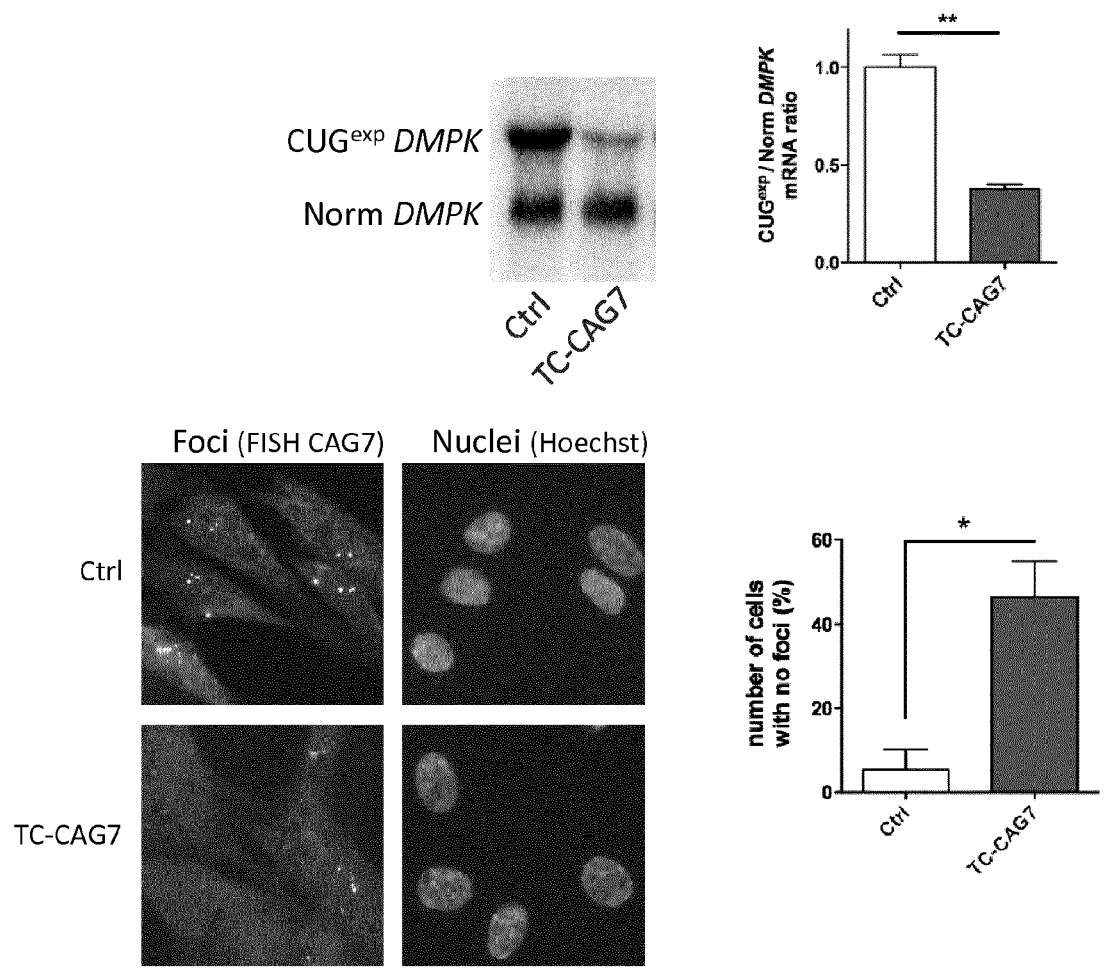

FIG. 17 presents an experiment showing the in vitro efficiency of a tc-DNA-PS oligonucleotide targeting CUG amplifications.

Figure 18:
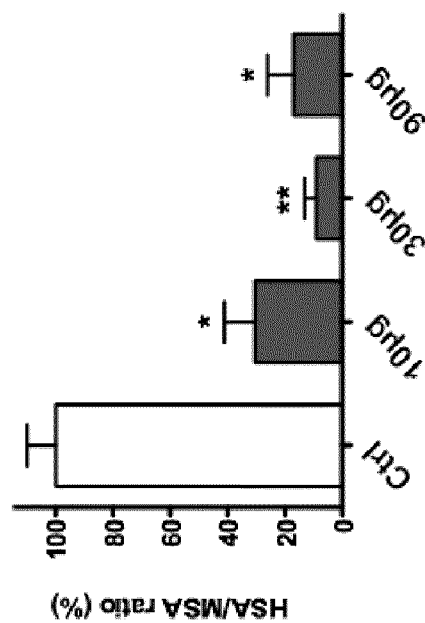
Figure 18:
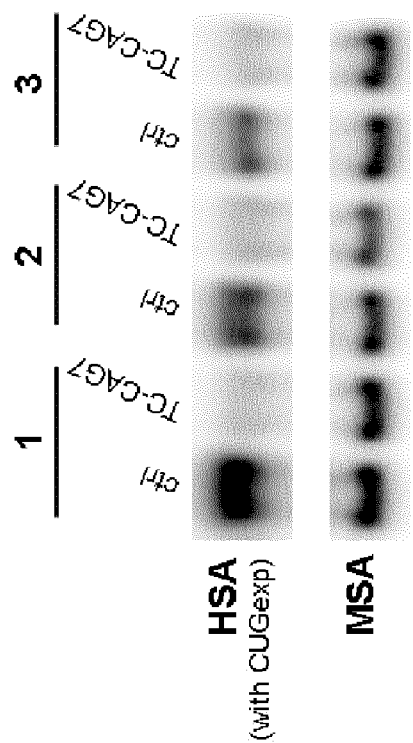
Figure 19:
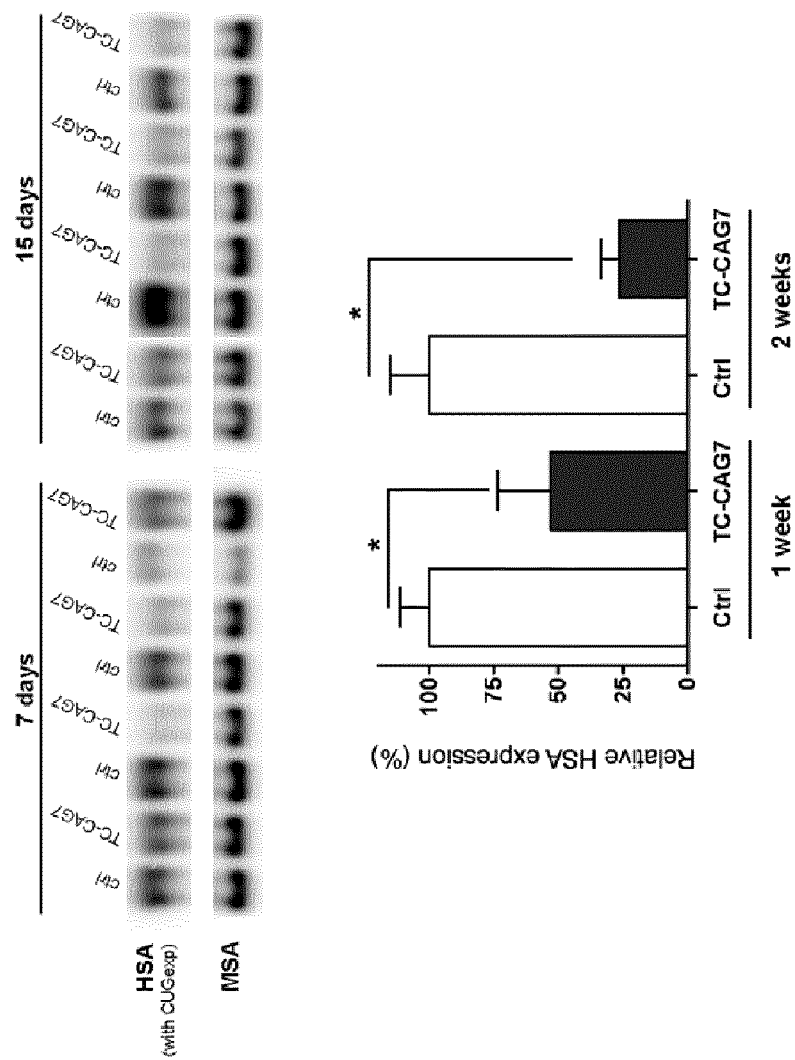
Figure 20:
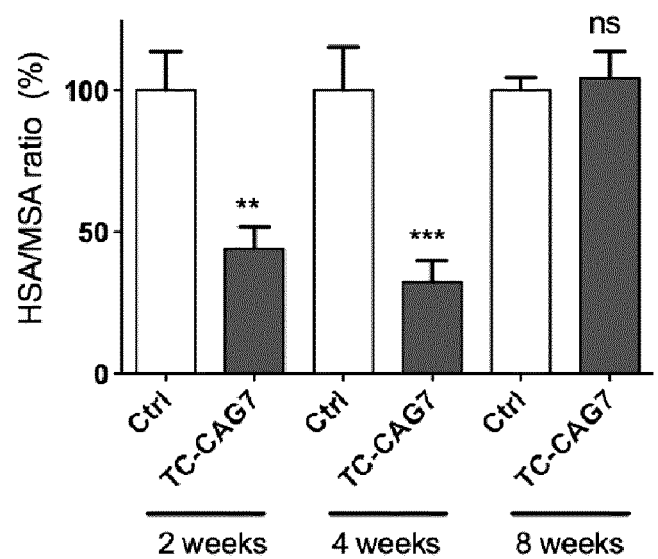

FIGS. 18 to 20 present experiment showing the in vivo efficiency of a tc-DNA-PS oligonucleotide targeting CUG amplifications.

DETAILED DESCRIPTION

The present invention is based upon the unexpected discovery that tricyclo-phosphorothioate DNA molecules, as exemplified by the tc-DNA-PS antisense oligonucleotide (AON) designated M23D(+02-13), can be delivered into cardiac cells and into the central nervous system (CNS) after intravenous administration to restore a mutated gene, such as a mutated dystrophin gene.

This discovery is quite surprising since the tricyclo-DNA version of the oligonucleotide (i.e. an oligonucleotide comprising classical phosphodiester linkages between tricyclo-nucleosides) is not as efficient in modifying gene expression in cardiac cells, or in the CNS after systemic administration. In addition, neither PMO nor 2'OMe-PS-RNA have been shown efficient in modifying gene expression in cardiac cells at doses acceptable for use in human subjects (Yokota, T et al Ann Neurol 2009; Mol. Ther. 2010 June; 18(6):1210-7. Preclinical PK and PD studies on 2'-O-methyl-phosphorothioate RNA antisense oligonucleotides in the mdx mouse model. Heemskerk H, de Winter C, van Kuik P, Heuvelmans N, Sabatelli P, Rimessi P, Braghetta P, van Ommen G J, de Kimpe S, Ferlini A, Aartsma-Rus A, van Deutekom J C.). For these chemistries, going into cardiac cells required either exceptionally high doses such as 3 g/kg-300 fold the dose used in clinical trials today (Gene Ther. 2010 January; 17(1):132-40. Dose-dependent restoration of dystrophin expression in cardiac muscle of dystrophic mice by systemically delivered morpholino. Wu B, Lu P, Benrashid E, Malik S, Ashar J, Doran T J, Lu Q L) or conjugated penetrating peptides or mechanical stress such as ultrasound (Mol. Ther. 2011 July; 19(7):1295-303. Pip5 transduction peptides direct high efficiency oligonucleotide-mediated dystrophin exon skipping in heart and phenotypic correction in mdx mice. Yin H, Saleh A F, Betts C, Camelliti P, Seow Y, Ashraf S, Arzumanov A, Hammond S, Merritt T, Gait M J, Wood M J; Ultrasound Med. Biol. 2009 June; 35(6):976-84. Microbubble stability is a major determinant of the efficiency of ultrasound and microbubble mediated in vivo gene transfer. Alter J, Sennoga C A, Lopes D M, Eckersley R J, Wells D J.)

The present discovery will find broad application in the treatment of genetic diseases, generally, and, more specifically, in the treatment of a neuromuscular or musculoskeletal disease such as Duchenne Muscular Dystrophy, Spinal Muscular Atrophy, and Steinert's Myotonic Dystrophy, and in the treatment of heart or CNS diseases.

Definitions

As used herein, the term "phosphorothioate linkage" refers to a 5' . . . —O—P(S)—O— . . . 3' moiety between two adjacent nucleosides in a nucleic acid molecule.

As used herein, the term "tricyclo-DNA (tc-DNA)" refers to a class of constrained DNA analogs in which each nucleotide is modified by the introduction of a cyclopropane ring to restrict conformational flexibility of the backbone and to optimize the backbone geometry of the torsion angle γ (Ittig et al., *Nucleic Acids Res.* 32:346-353 (2004); Ittig et al., Prague, Academy of Sciences of the Czech Republic. 7:21-26 (Coll. Symp. Series, Hocec, M., 2005); Ivanova et al., *Oligonucleotides* 17:54-65 (2007); Renneberg et al., *Nucleic Acids Res.* 30:2751-2757 (2002); Renneberg et al., *Chembiochem.* 5:1114-1118 (2004); and Renneberg et al., *JACS.* 124:5993-6002 (2002)). Homobasic adenine- and thymine-containing tc-DNAs form extraordinarily stable A-T base pairs with complementary RNAs.

As used herein, the term "tricyclo-nucleoside" refers to a subunit of a nucleic acid molecule having the following formula:

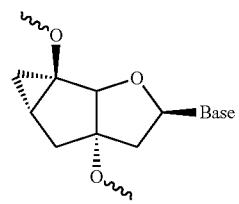

As used herein, the term "antisense oligonucleotide (AON)" refers to an oligonucleotide that is capable of interacting with and/or hybridizing to a pre-mRNA or an mRNA having a complementary nucleotide sequence thereby modifying gene expression.

As used herein, a "base" refers to typical DNA and RNA bases (uracil, thymine, adenine, guanine and cytosine), and modified bases or base analogs (e.g., 5-methyl cytosine, 5-bromouracil or inosine). A base analog is a chemical whose molecular structure mimics that of a typical DNA or RNA base.

As used herein, "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. In reference to the tc-DNA-PS AON of the present disclosure, the binding free energy for a tc-DNA-PS AON with its complementary sequence is sufficient to allow the relevant function of the tc-DNA-PS AON to proceed and there is a sufficient degree of complementarity to avoid non-specific binding of the tc-DNA-PS AON to non-target sequences under conditions in which specific binding is desired, i.e., under physiological conditions in the case of ex vivo or in vivo therapeutic treatment. Determination of binding free energies for nucleic acid molecules is well known in the art (see e.g., Turner et al., *CSH Symp. Quant. Biol. LII*:123-133 (1987); Freier et al., *Proc. Nat. Acad. Sci. USA* 83:9373-77 (1986); and Turner et al., *J. Am. Chem. Soc.* 109:3783-3785 (1987)). Thus, "complementary" (or "specifically hybridizable") are terms that indicate a sufficient degree of complementarity or precise pairing such that stable and specific binding occurs between a tc-DNA-PS AON and a pre-mRNA or mRNA target.

It is understood in the art that a nucleic acid molecule need not be 100% complementary to a target nucleic acid sequence to be specifically hybridizable. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

As used herein, the terms "precursor mRNA" or "pre-mRNA" refer to an immature single strand of messenger ribonucleic acid (mRNA) that contains one or more intervening sequence(s) (introns). Pre-mRNA is transcribed by an RNA polymerase from a DNA template in the cell nucleus and is comprised of alternating sequences of introns and coding regions (exons). Once a pre-mRNA has been completely processed by the splicing out of introns and joining of exons, it is referred to as "messenger RNA" or "mRNA," which is an RNA that is comprised exclusively of exons. Eukaryotic pre-mRNAs exist only transiently before being fully processed into mRNA. When a pre-mRNA has been properly processed to an mRNA sequence, it is exported out of the nucleus and eventually translated into a protein by ribosomes in the cytoplasm.

As used herein, the terms "splicing" and "processing" refers to the modification of a pre-mRNA following transcription, in which introns are removed and exons are joined. Splicing occurs in a series of reactions that are catalyzed by a large RNA-protein complex composed of five small nuclear ribonucleoproteins (snRNPs) referred to as a spliceosome. Within an intron, a 3' splice site, a 5' splice site, and a branch site are required for splicing. The RNA components of snRNPs interact with the intron and may be involved in catalysis.

Pre-mRNA splicing involves two sequential biochemical reactions. Both reactions involve the spliceosomal transesterification between RNA nucleotides. In a first reaction, the 2'-OH of a specific branch-point nucleotide within an intron, which is defined during spliceosome assembly, performs a nucleophilic attack on the first nucleotide of the intron at the 5' splice site forming a lariat intermediate. In a second reaction, the 3'-OH of the released 5' exon performs a nucleophilic attack at the last nucleotide of the intron at the 3' splice site thus joining the exons and releasing the intron lariat. Pre-mRNA splicing is regulated by a number of factors such as exonic splice enhancer or inhibitor sequences, and in particular also by intronic silencer sequences (ISS) and terminal stem loop (TSL) sequences.

As used herein, the terms "intronic silencer sequences (ISS)" and "terminal stem loop (TSL)" refer to sequence elements within introns and exons, respectively, that control alternative splicing by the binding of trans-acting protein factors within a pre-mRNA thereby resulting in differential use of splice sites. Typically, intronic silencer sequences are between 8 and 16 nucleotides and are less conserved than the splice sites at exon-intron junctions. Terminal stem loop sequences are typically between 12 and 24 nucleotides and form a secondary loop structure due to the complementarity, and hence binding, within the 12-24 nucleotide sequence.

By "subject" is meant an organism, which is a donor or recipient of explanted cells or the cells themselves. "Subject" also refers to an organism to which the nucleic acid molecules of this disclosure can be administered. In one embodiment, a subject is a mammal or mammalian cell. In another embodiment, a subject is a human or human cell.

As used herein, the term "therapeutically effective amount" means an amount of tc-DNA-PS molecule (e.g an AON) that is sufficient, in the subject (e.g., human) to which it is administered, to treat or prevent the stated disease, disorder, or condition. The tc-DNA-PS molecule of the instant invention, individually, or in combination or in conjunction with other drugs, can be used to treat diseases or conditions, in particular those discussed herein. For example, to treat a particular disease, disorder, or condition, the tc-DNA-PS can be administered to a patient or can be administered to other appropriate cells evident to those skilled in the art, individually or in combination with one or more drugs, under conditions suitable for treatment.

As used herein, the phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the European or U.S. Pharmacopeia or other generally recognized pharmacopeia for use in animals, and more particularly in humans.

As used herein, the term "isolated" means that the referenced material is removed from its native environment, e.g., a cell. Thus, an isolated biological material can be free of some or all cellular components, i.e. components of the cells in which the native material occurs naturally (e.g., cytoplasmic or membrane component).

The term "purified" as used herein refers to material that has been isolated under conditions that reduce or eliminate the presence of unrelated materials, i.e. contaminants, including native materials from which the material is obtained. For example, a purified tc-DNA-PS molecule is preferably substantially free of cell or culture components, including tissue culture components, contaminants, and the like. As used herein, the term "substantially free" is used operationally, in the context of analytical testing of the material. Preferably, purified material substantially free of contaminants is at least 50% pure; more preferably, at least 90% pure, and more preferably still at least 99% pure. Purity can be evaluated by chromatography, gel electrophoresis, immunoassay, composition analysis, biological assay, and other methods known in the art.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, "about" or "consisting essentially of" mean±20% of the indicated range, value, or structure, unless otherwise indicated.

As used herein, the terms "include" and "comprise" are used synonymously. It should be understood that the terms "a" and "an" as used herein refer to "one or more" of the enumerated components. The use of the alternative (e.g., "or") should be understood to mean either one, both, or any combination thereof of the alternatives.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

In the nomenclature used herein for designating AONs, such as in M23D(+02-13), M means Mouse, 23 is the exon id, D means Donor site at the 3' end of the exon, +2 indicates that the antisense starts within the exon, 2 nucleotide before the D site, -13 indicates that the antisense ends at the 13$^{th}$ nucleotide of the downstream intron.

Tricyclo-Phosphorothioate DNA Molecules of the Invention and Compositions Containing the Same An object of the invention relates to a nucleic acid molecule comprising tricyclo-nucleosides joined by internucleoside phosphorothioate linkages (3'-OPS—O-5' linkages), also referred to as "tricyclo-phosphorothioate DNA" or "tc-DNA-PS" in the present disclosure.

The nucleic acid molecule of the invention stems from the improvement of the chemistry of tricyclo-nucleoside-containing DNA, where phosphodiester linkages are replaced by phosphorothioate linkages.

According to the present disclosure, a nucleic acid of the invention comprises at least two adjacent tricyclo-nucleosides joined by a phosphorothioate linkage. This sequence of moieties has never been disclosed before the present study. It will be understood that the nucleic acid molecule of the invention can also comprise nucleosides with different chemistry such as classical ribose- or deoxyribose-containing nucleosides, LNA nucleosides and the like. The nucleic acid molecule of the invention can also contain other types of internucleoside linkages, in addition to phosphorothioate linkage, for example classical phosphodiester linkage. However, the invention preferentially relates to nucleic acid molecules where the proportion of tricyclo-nucleosides represent at least 50%, preferentially at least 60%, 70%, 80%, 90% or 95% of total nucleosides in the nucleic acid molecule. In addition, the invention preferentially relates to nucleic acid molecules where the proportion of internucleoside phosphorothioate linkages represent at least 50%, preferentially at least 60%, 70%, 80%, 90% or 95% of total internucleoside linkages in the nucleic acid molecule. In a particular embodiment, all the nucleosides in the nucleic acid molecule of the invention are tricyclo-nucleosides. In another embodiment, all the intersubunit linkages are phosphorothioate linkages.

In a particularly preferred embodiment, the nucleic acid molecule of the invention is a tricyclo-phosphorothioate nucleic acid molecule comprising nucleosides subunits joined by intersubunit linkages, wherein all the nucleosides are tricyclo-nucleosides and all the intersubunit linkages are phosphorothioate linkages.

The nucleoside subunits comprised in the nucleic acid of the invention can be selected to be in a defined sequence, such as a sequence of bases capable of hybridizing specifically to a single-strand nucleic acid target sequence or a sequence that will allow formation of a triplex structure between the nucleic acid of the invention and a target nucleic acid duplex. The target nucleic acid sequences can be RNA and DNA sequences. When desirable, the nucleic acids of the present invention can be labeled with a reporter group, such as radioactive labels, biotin labels, fluorescent labels and the like, to facilitate the detection of the nucleic acid itself and its presence in, for example, hybridization complexes.

The size of the nucleic acid molecule of the invention will depend on the particular use it is prepared for. For example, the tc-DNA-PS molecule of the invention can be at least 3 nucleotide long, in particular at least 5, 10, 20, 30, 40 or 50 nucleotide long. In a particular embodiment, the tc-DNA-PS molecule of the invention comprises between 3 and 50 nucleotides, in particular between 5 and 21 nucleotides, in particular between 6 and 18 nucleotides. Interestingly, tc-PS DNA oligonucleotides can be abridged to 15 mer, while PMO morpholino and 2'O-Me-PS-RNA are usually made of 24 and 20 mer, respectively. Therefore, the invention relates in particular to tc-DNA-PS molecules comprising, or consisting of, 15 nucleotides. In a further particular embodiment, the nucleic acid molecule of the invention comprises between 3 and 20 nucleotides, in particular between 10 and 15 nucleotides.

The synthesis of tricyclo-nucleosides is known in the art, for example as described in Steffens, R. and Leumann, C. (1997) Nucleic-acid analogs with constraint conformational flexibility in the sugar-phosphate backbone "Tricyclo-DNA". Part 1. Preparation of [(5'R,6'R)-2-deoxy-3',5'-ethano-5',6'-methano-β-D-ribofuranosyl]thymine and -adenine, and the corresponding phosphoramidites for oligonucleotide synthesis. *Helv. Chim. Acta*, 80, 2426-2439 and in Renneberg, D. and Leumann, C. J. (2002) Watson-Crick base-pairing properties of tricyclo-DNA. *J. Am. Chem. Soc.*, 124, 5993-6002.

The synthesis of phosphorothioate tc-DNA follows classical procedures in solid phase oligonucleotide synthesis according to the phosphoramidite approach (Oligonucleotide Synthesis—A Practical Approach, Oxford University Press, Oxford, 1984). In the method of synthesis of the present invention, a first tricyclo-nucleoside is bound to a solid phase support (for example to a long chain alkylamine controlled pore glass (LCAA-CPG) via a succinyl linker). The first nucleotide has additionally a protected 5'-OH group (e.g. dimethoxytrityl-DMT-group). The protected 5' group is then deprotected to form a free 5'-OH group to which a second nucleotide is added. The free 5'-OH group of the first nucleotide is reacted with a 5'-protected tricyclonucleoside-3'-O-cyanoethyl-N,N-diisopropylaminophosphoramidite.

The internucleoside phosphoramidite group is then sulfurized to form a phosphorothioate internucleoside linkage between the first and second tricyclo-nucleosides. Non reacted 5'-OH groups of the first nucleotide are esterified (capped) to prevent the synthesis of failure sequences. This sequence is then repeated to add a further tc-PS nucleotide as many times as necessary to form the complete desired nucleic acid sequence.

A particular embodiment of the method of synthesis of a nucleic acid according to the invention is described below, with reference to scheme 1.

Scheme 1: General protocol for the synthesis of tricyclo-phosphorothioate-DNA (tc-DNA-PS)

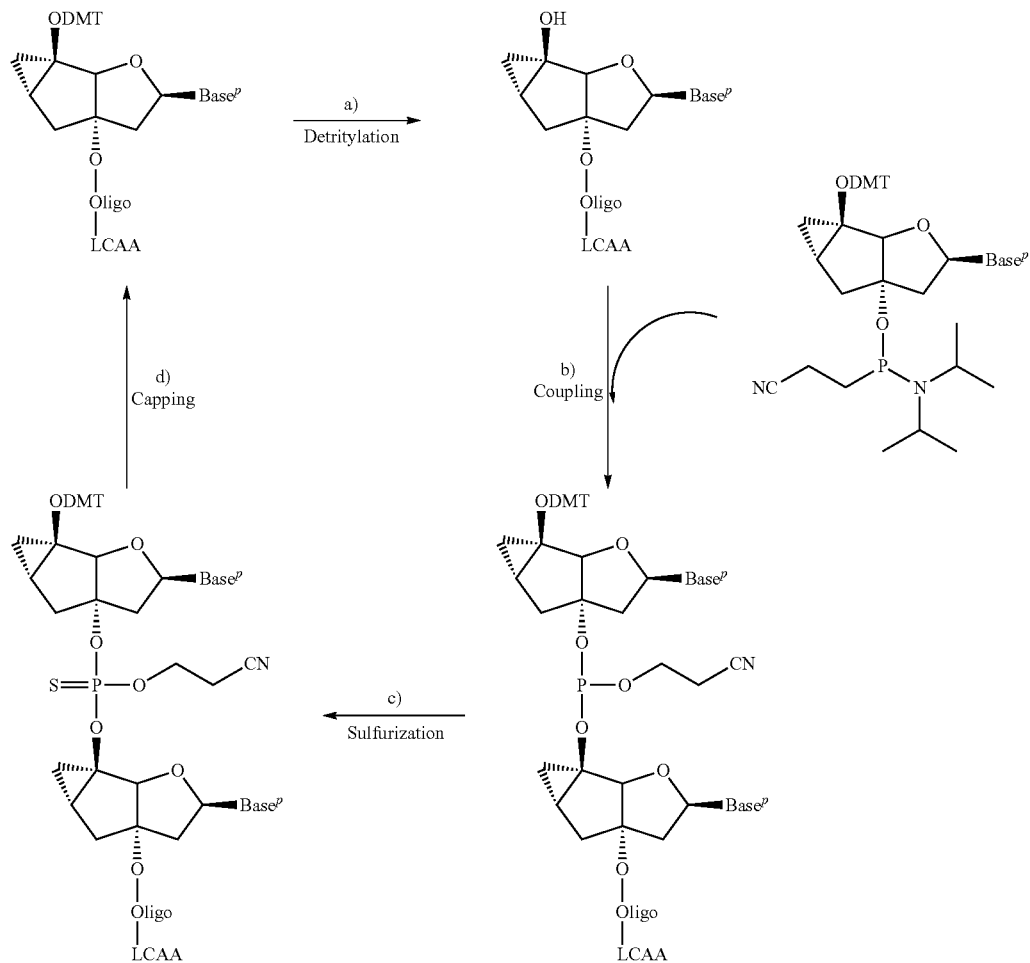

The synthesis cycle in which one additional unit is attached to the growing chain consists of four sequential steps (a-d). After chain assembly the oligonucleotide is detached from the solid support and deprotected in the usual way (conc $NH_3$, 55° C., 16 h). Long chain alkylamine controlled pore glass (LCAA-CPG), to which the first tricyclo-nucleoside is bound via a succinyl linker, is used as solid support. Syntheses were generally performed on the 1.3 or 10 mmol scale on a Pharmacia gene assembler plus DNA synthesizer. Tricyclo-phosphorothioate-oligonucleotides are synthesized with a 5' terminal phosphate or thiophosphate group to ensure chemical stability of the 5'-end (R. Steffens and C. J. Leumann, J. Am. Chem. Soc., 1999, 121, 3249-3255). The conditions for each step a)-d) are given below and are optimized for a 10 µmol synthesis.

a) Detritylation:

Flush with 3% dichloroacetic acid in 1,2-dichloroethane (DCE) for 1.5 min. Then wash with DCE and $CH_3CN$.

b) Coupling:

Phosphoramidite solution (0.1 µM in $CH_3CN$*, 400 µL) and activator 5-ethylthiotetrazol (ETT, 0.25M in $CH_3CN$, 600 µL) is applied to the solid support. Coupling time: 9 min. Then wash with $CH_3CN$.

*$CH_3CN$ is used for building blocks tc-T, tc-G and tc-C. For solubility reasons building block tc-A is used in dry DCE as solvent.

c) Sulfurization:

Bis(phenylacetyl)disulfide (PADS) in dry pyridine/$CH_3CN$ 1/1 (0.2M) is flushed over the solid support for 3 min. Then wash with $CH_3CN$ d) Capping:

Unreacted 5'-hydroxyl groups are capped using CapA (4-dimethylaminopyridine (DMAP, 0.5M) in $CH_3CN$) and CapB solution (acetic anhydride ($AC_2O$), collidine in $CH_3CN$ (2:3:5)) for 20 s each. Then wash with $CH_3CN$.

The tc-DNA phosphoramidite building blocks used for the synthesis of the nucleic acid molecule of the invention may be synthesized as described in Steffens and Leumann, C. Helv. Chim. Acta 80:2426-2439 (1997). Chain-extension cycles may be essentially identical to those for natural oligodeoxynucleotide synthesis. See, Pharmacia LKB User's Manual (56-1111-56) (Gene Assembler Special/4 Primers).

The tc-DNA-PS molecule of the invention can be an antisense oligonucleotide complementary to a portion of an RNA encoded by a gene, in particular a human gene. The present invention thus also relates to a tricyclo-phosphorothioate DNA antisense oligonucleotide.

The tc-DNA-PS molecule (or antisense oligonucleotide) of the invention may be designed in particular:
for effecting exon skipping, in particular for skipping one or more exons in a dystrophin gene;

for facilitating inclusion of an exon during the processing of a target pre-mRNA, in particular for facilitating inclusion of exon 7 during processing of an SMN2 pre-mRNA;

for targeting a mutated mRNA comprising excess CUG amplifications to prevent sequestration of nuclear proteins to the expanded CUG repeats, for example for targeting a mutated DM1 mRNA comprising excess CUG amplifications;

for facilitating the destruction of a mutated mRNA comprising excess CUG amplifications, for example facilitating the destruction of a mutated DM1 mRNA comprising excess CUG amplifications.

Tc-DNA-PS molecules of the present invention can be formulated in a composition, with a carrier. The composition can be a pharmaceutical composition, with the carrier being a pharmaceutically acceptable carrier.

Thus, the invention also relates to a pharmaceutical composition comprising a nucleic acid of the invention, which is in particular an antisense oligonucleotide complementary to a portion of an RNA encoded by a gene, in particular a human gene, and wherein said composition further comprises a pharmaceutically acceptable carrier. In addition, the invention also relates to a nucleic acid molecule of the invention, in combination with another therapeutic agent. The nucleic acid molecule of the invention and the other therapeutic agent can be formulated into a pharmaceutical composition, or are part of a combined preparation (kit-of-parts), for simultaneous, separate or sequential use. The person skilled in the art will adapt the other therapeutic agent and the sequence of the nucleic acid of the invention to the particular disease sought to be treated.

Tc-DNA-PS molecules described herein may be in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Aqueous suspensions may also contain one or more preservatives, for example ethyl, or n-propyl p-hydroxybenzoate. Dispersible powders and granules suitable for preparation of an aqueous suspension by the addition of water provide the active ingredient in admixture with a dispersing or wetting agent, suspending agent and one or more preservatives.

According to a particular embodiment, the invention relates to a composition comprising a tc-DNA-PS molecule as described above and a pharmaceutically acceptable carrier, the composition being an injectable composition. Tc-DNA-PS compositions may be in the form of a sterile injectable aqueous or oleaginous suspension. Suspensions may be formulated according to the known art using those suitable dispersing or wetting agents and suspending agents that have been mentioned above. The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono or diglycerides. In addition, fatty acids such as oleic acid find use in the preparation of injectables.

The present disclosure also includes compositions prepared for storage or administration that include a pharmaceutically effective amount of the desired tc-DNA-PS molecule of the invention in a pharmaceutically acceptable carrier or diluent. Acceptable carriers or diluents for therapeutic use are well known in the pharmaceutical art, and are described, for example, in *Remington's Pharmaceutical Sciences* (Mack Publishing Co., A. R. Gennaro edit., 1985). For example, preservatives and stabilizers can be provided. These include sodium benzoate, sorbic acid and esters of p-hydroxybenzoic acid. In addition, antioxidants and suspending agents can be used.

The present disclosure also provides compositions and methods for facilitating exon skipping or masking intronic silencing or terminal stem loops in a pre-mRNA or for targeting the destruction of mRNA in a cell or organism. In related embodiments, this disclosure provides methods and compositions comprising a tc-DNA-PS molecule according to the invention for treating a subject, including a human cell, tissue or individual, having a disease or at risk of developing a disease, in particular one of the specific diseases as described herein. In one embodiment, the method includes administering a tc-DNA-PS molecule of the present invention or a pharmaceutical composition containing the tc-DNA-PS molecule to a cell or an organism, such as a mammal, such that the processing of a pre-mRNA is modified or the destruction of an mRNA is targeted. Mammalian subjects amenable for treatment using the compositions and methods of the present invention include those suffering from one or more disorders which are amenable to such treatment such as, for example, Duchenne Muscular Dystrophy, Spinal Muscular Atrophy, or Steinert's Myotonic Dystrophy.

The tc-DNA-PS compositions of the instant disclosure can be effectively employed as pharmaceutically acceptable formulations. Pharmaceutically-acceptable formulations prevent, alter the occurrence or severity of, or treat (alleviate one or more symptom(s) to a detectable or measurable extent) of a disease state or other adverse condition in a patient. A pharmaceutically acceptable formulation includes salts of the above compounds, e.g., acid addition salts such as salts of hydrochloric acid, hydrobromic acid, acetic acid, and benzene sulfonic acid. A pharmaceutical composition or formulation refers to a composition or formulation in a form suitable for administration, e.g., systemic administration, into a cell or patient such as a human. Suitable forms, in part, depend upon the use or the route of entry, for example transdermal or by injection. Such forms should not prevent the composition or formulation from reaching a target cell (i.e. a cell to which the tc-DNA-PS molecule is desirable for delivery). For example, pharmaceutical compositions injected into the blood stream should be soluble. Other factors are known in the art, and include considerations such as toxicity and forms that prevent the composition or formulation from exerting its effect.

Pharmaceutical compositions of this disclosure can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate.

The tc-DNA-PS molecule of this disclosure may be administered to a patient by any standard means, with or without stabilizers, buffers, or the like, to form a composition suitable for treatment. When it is desired to use a liposome delivery mechanism, standard protocols for formation of liposomes can be followed. Thus nucleic acid molecules of the present disclosure may be administered in any form, for example transdermally or by local, oral, rectal, intramuscular, intracardiac, intraperitoneal, loco-regional, systemic (for example intravenously or intra-arterially), or intrathecal injection.

This disclosure also features the use of compositions comprising surface-modified liposomes containing poly(ethylene glycol) lipids (PEG-modified, or long-circulating liposomes or stealth liposomes). These formulations offer a method for increasing the accumulation of the tc-DNA-PS molecule of the invention in target tissues. This class of drug carriers resists opsonization and elimination by the mononuclear phagocytic system (MPS or RES), thereby enabling longer blood circulation times and enhanced tissue exposure for the encapsulated tc-DNA-PS molecule (Lasic et al., *Chem. Rev.* 95:2601-2627 (1995) and Ishiwata et al., *Chem. Pharm. Bull.* 43:1005-1011 (1995). Long-circulating liposomes enhance the pharmacokinetics and pharmacodynamics of nucleic acid molecules, particularly compared to conventional cationic liposomes which are known to accumulate in tissues of the MPS (Liu et al., *J. Biol. Chem.* 42:24864-24870 (1995); Choi et al., PCT Publication No. WO 96/10391; Ansell et al., PCT Publication No. WO 96/10390; Holland et al., PCT Publication No. WO 96/10392). Long-circulating liposomes are also likely to protect the tc-DNA-PS molecules of the invention from nuclease degradation to a greater extent compared to cationic liposomes, based on their ability to avoid accumulation in metabolically aggressive MPS tissues such as the liver and spleen.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. For example, an amount between 0.1 mg/kg and 100 mg/kg body weight/day of active ingredients is administered dependent upon potency of the tc-DNA-PS molecule of this disclosure.

Dosage levels of the order of from about 0.1 mg to about 140 mg per kilogram of body weight per week are useful in the treatment of the conditions indicated herein (about 0.5 mg to about 7 g per patient per week). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient depends upon a variety of factors including the activity of the specific compound employed, the age, body weight, general health, sex, diet, time of administration, route of administration, and rate of excretion, drug combination and the severity of the particular disease undergoing therapy. Following administration of compositions according to the formulations and methods of this disclosure, test subjects will exhibit about a 10% up to about a 99% reduction in one or more symptoms associated with the disease or disorder being treated, as compared to placebo-treated or other suitable control subjects.

The tc-DNA-PS molecule of the invention can be administered to cells by a variety of methods known to those of skill in the art, including administration within formulations that comprise the tc-DNA-PS molecule alone, or that further comprise one or more additional components, such as a pharmaceutically acceptable carrier, diluent, excipient, adjuvant, emulsifier, buffer, stabilizer, preservative, or the like. In certain embodiments, the tc-DNA-PS molecule of the invention can be encapsulated in liposomes, administered by iontophoresis, or incorporated into other vehicles, such as hydrogels, cyclodextrins, biodegradable nanocapsules, bioadhesive microspheres, or proteinaceous vectors (see, e.g., PCT Publication No. WO 00/53722).

Direct injection of the tc-DNA-PS molecule of this disclosure, whether intravenous, subcutaneous, intramuscular, or intradermal, can take place using standard needle and syringe methodologies, or by needle-free technologies, such as those described in Conry et al., *Clin. Cancer Res.* 5:2330-2337 (1999), and PCT Publication No. WO 99/31262.

Further methods for delivery of nucleic acid molecules are described, for example, in Boado et al., *J. Pharm. Sci.* 87:1308-1315 (1998); Tyler et al., *FEBS Lett.* 421:280-284 (1999); Pardridge et al., *Proc. Nat'l Acad. Sci. USA* 92:5592-5596 (1995); Boado, *Adv. Drug Delivery Rev.* 15:73-107 (1995); Aldrian-Herrada et al., *Nucleic Acids Res.* 26:4910-4916 (1998); Tyler et al., *Proc. Nat'l Acad. Sci. USA* 96:7053-7058 (1999); Akhtar et al., *Trends Cell Bio.* 2:139 (1992); "Delivery Strategies for Antisense Oligonucleotide Therapeutics," (ed Akhtar, 1995); Maurer et al., *Mol. Membr. Biol.* 16:129-140 (1999); Hofland and Huang, *Handb. Exp. Pharmacol* 137:165-192 (1999); and Lee et al., *ACS Symp. Ser.* 752:184-192 (2000). These protocols can be utilized to supplement or complement delivery of virtually any tc-DNA-PS molecule contemplated within this disclosure.

Methods of Treatment

As mentioned above, the nucleic acid molecule of the present invention can be an antisense oligonucleotide (AON) designed in order to be complementary of a specific mRNA or pre-mRNA. The antisense oligonucleotides of the invention can be used for the treatment of numerous diseases, a number of which are described below. Of course, the illustrative diseases provided below do not limit the invention, and the new chemistry provided herein may be used for the treatment of any disease the skilled person would envision to be treatable by the administration of an AON.

Tricyclo-Phosphorothioate Antisense Oligonucleotides for the Treatment of Duchenne Muscular Dystrophy Within certain embodiments, the present disclosure provides AONs that may be suitably employed for the treatment of Duchenne Muscular Dystrophy (DMD), a severe recessive x-linked form of muscular dystrophy that is characterized by rapid progression of muscle degeneration, eventually leading to loss in ambulation, paralysis, and death. DMD is caused by a mutation, such as a non-sense or frame-shift mutation, within the dystrophin gene, which is located on the human X chromosome. The dystrophin gene encodes the dystrophin protein, an important structural component within muscle tissue which provides structural stability to muscle fibre sarcolemma as well as to the dystroglycan complex (DGC), located at the cell membrane. A non-sense or frame-shift mutation may result in premature termination of translation and, hence, a C-terminally truncated, non-functional dystrophin protein.

DMD caused by one or more stop mutation(s) or frameshift mutation(s) can be relieved by excising one or several exons so as to restore the translational reading frame and thereby restoring the mRNA sequence downstream of the mutation. To achieve this, as part of the present disclosure, nucleic acid molecules according to the invention were developed as antisense AONs to target regions within the pre-mRNA that can mask spliceosomal recognition of one or more exon(s). By targeting these regions with tc-DNA-PS AONs, exons may be removed via alternative splicing to yield mature, internally partially deleted but functional dystrophin mRNA.

Thus, the tc-DNA-PS AON described herein are effective in facilitating the skipping of one or more mutated exons in a dystrophin gene during the processing of a dystrophin pre-mRNA thereby restoring the proper reading frame of the resulting dystrophin mRNA, which, when translated, yields a semi-functional dystrophin protein. Thus, the tc-DNA-PS AON disclosed herein may be used therapeutically for patients afflicted with DMD.

As used herein, the term "exon skipping" refers to the modification of pre-mRNA splicing by the targeting of splice donor and/or acceptor sites within a pre-mRNA with one or more complementary antisense oligonucleotide(s) (AONs). By blocking access of a spliceosome to one or more splice donor or acceptor sites, or indeed any other site within an exon or intron involved in the definition of splicing, an AON can prevent a splicing reaction thereby causing the deletion of one or more exons from a fully-processed mRNA. Exon skipping is achieved in the nucleus during the maturation process of pre-mRNAs. It includes the masking of key sequences involved in the splicing of targeted exons by using antisense oligonucleotides (AON) that are, for example, complementary to splice donor sequences within a pre-mRNA. The tc-DNA-PS AON provided herein may be suitably employed for exon skipping through the masking of splice sites at intron/exon junctions within a dystrophin pre-mRNA thereby facilitating the deletion of a mutant exon during the processing of the pre-mRNA to a mature mRNA.

For example, a non-sense or frameshift mutation within exon 23 or exon 50 of a dystrophin gene yields a carboxy-terminally truncated, non-functional dystrophin protein. By hybridizing to nucleotides comprising a dystrophin pre-mRNA splice donor site in intron 23 or intron 51, respectively, and adjacent 5' nucleotides of exon 23 or exon 51, tc-DNA-PS AON disclosed herein are capable of preventing the inclusion of the mutated exon 23 or exon 51 into the mature mRNA transcript. The expression of that mature mRNA transcript yields a semi-functional dystrophin protein that is deleted in the amino acids encoded by exon 23 or exons 50 and 51 but that includes dystrophin amino acids both N-terminal and C-terminal to those deleted amino acids.

The tc-DNA-PS AON disclosed herein for skipping an exon during processing of a dystrophin pre-mRNA typically contain between 6-22 contiguous tricyclo-PS nucleotides, in particular between 8-20 tricyclo-PS nucleotides, more particularly between 10 and 18 contiguous tricyclo-PS nucleotides, wherein 6-16 nucleotides, in particular 8-16 nucleotides of the tc-DNA-PS AON are complementary to a dystrophin pre-mRNA intronic splice donor site, wherein 2-8 nucleotides of the tc-DNA-PS AON are complementary to a dystrophin pre-mRNA exonic region, and wherein the intronic splice donor site is contiguous with and 5' to the exonic region. Depending upon the precise application contemplated, tc-DNA-PS AON may be between 12 and 16 nucleotides or between 13 and 15 nucleotides and may comprise between 6 and 14 nucleotides that are complementary to the intronic splice donor site and between 2 and 5 nucleotides that are complementary to the exonic region.

Exemplified herein are tc-DNA-PS AON designed for skipping a mutated exon 23 within a dystrophin pre-mRNA. The tc-DNA AON comprise the nucleotide sequence 5'-AACCTCGGCTTACCT-3' (M23D (+02-13), SEQ ID NO: 1) and specifically hybridize to nucleotides at the 3' end of dystrophin pre-mRNA intron 23 and to nucleotides at the contiguous 5' end of dystrophin pre-mRNA exon 23. An alternative AON that can be used is sequence 5'-GGC-CAAACCTCGGCTTACCT-3' (M23D (+2-18), SEQ ID NO:2).

Also provided are tc-DNA-PS AON designed for skipping a mutated exon 51 within a dystrophin pre-mRNA. The tc-DNA AON comprise a nucleotide sequence selected from the group consisting of 5'-AGAAATGCCATCTTC-3' (H51 (+68+82), SEQ ID NO: 3), 5'-AAATGCCATCT-TCCT-3' (H51 (+70+84), SEQ ID NO: 4), 5'-TGCCATCT-TCCTTGA-3' (H51 (+73+87), SEQ ID NO: 5) and 5'-GCA-GTTTCCTTAGTAA-3' (H51 (+40+55), SEQ ID NO: 6), and specifically hybridize to nucleotides at the 3' end of dystrophin pre-mRNA exon 51 and to nucleotides at the 5' end of dystrophin pre-mRNA exon 51.

Tricyclo-Phosphorothioate DNA Antisense Oligonucleotides for the Treatment of Spinal Muscular Atrophy Within other embodiments, the present disclosure provides tc-DNA-PS AON that may be suitably employed for the treatment of Spinal Muscular Atrophy (SMA). SMA is caused by mutations in both copies of the SMN1 gene, which in a normal cell is characterized by the presence of exons 7 and 8 in fully-processed mRNA. A second gene present in the human in variable copy numbers, SMN2, carries a silent mutation in exon 7 which alters an exonic splice enhancer sequence. As a consequence, splicing of SMN2 is altered compared to SMN1 and only 10% of a normal full-length SMN protein is transcribed from this gene while other non-functional SMN2 transcripts are deleted for exon 7. The low abundance of the normal full-length transcript of SMN2 cannot fully compensate for the lack of the SMN1-transcript, thereby causing the disease. By masking an intronic silencing sequence (ISS) and/or a terminal stem loop (TSL) within an SMN2 pre-mRNA, tc-DNA-PS AON described herein are expected to be capable of facilitating the inclusion of SMN2 exon 7 into a processed SMN2 pre-mRNA, which is translated into a fully functional SMN2 protein that is identical to the SMN1 protein and therefore capable of compensating for the loss of functional SMN1 protein. When expressed in vivo, the increased amounts of SMN2 protein can at least partially reverse Spinal Muscular Atrophy that is caused by mutations in the SMN1 gene.

Thus, the present disclosure provides tc-DNA-PS AON for facilitating the inclusion of exon 7 during processing of an SMN2 pre-mRNA wherein the tc-DNA-PS AON is 6-22 tricyclo nucleotides in length, in particular between 8-20 tricyclo nucleotides, more particularly between 10-18 tricyclo nucleotides in length and wherein the tc-DNA-PS AON is complementary to an SMN2 pre-mRNA intronic silencer sequence (ISS) or a terminal stem-loop (TSL). Such tc-DNA-PS AON may be between 13 and 17 nucleotides, between 12 and 16 nucleotides, or between 13 and 15 nucleotides.

Exemplified herein are tc-DNA AON that comprise the 15-nucleotide sequence 5'-CTTTCATAATGCTGG-3' (SMN2i7(10;25), SEQ ID NO: 7), which tc-DNA AON are complementary to an SMN2 pre-mRNA ISS and which may be employed to facilitate the inclusion of exon 7 into a processed SMN2 mRNA. Also exemplified herein are tc-DNA-PS AON that comprise the 13-nucleotide sequence 5'-TTAATTTAAGGAA-3' (SMN2e7(39;51), SEQ ID NO: 8), which tc-DNA-PS AON are complementary to an SMN2 pre-mRNA TSL2 and which may also be employed to facilitate the inclusion of exon 7 into a processed SMN2 mRNA.

Tricyclo-Phosphorothioate DNA Antisense
Oligonucleotides for the Treatment of Steinert's
Myotonic Dystrophy Within still further embodiments, the present disclosure provides tc-DNA-PS AON that may be suitably employed for the treatment of Steinert's Myotonic Dystrophy that results from CUG amplifications at the 3' end of the mRNA encoding DM1. It is believed that mutated DM1 mRNAs that contain excessive CUG amplifications are sequestered into the nucleus and accumulate to form nuclear foci. These foci are stable and are thought to bind to factors involved in the splicing machinery thereby widely affecting the transcriptome. As part of the present disclosure, it is expected that tc-DNA-PS AON may be employed to target the CUG sequences and facilitate the destruction of the mutated DM1 mRNA and/or prevent the sequestration of nuclear proteins to the expanded CUG repeats thereby leading to the release of the splicing factors and removal of the nuclear foci. Without being bound to a particular mechanistic theory, it is further believed that the tc-DNA-PS AON disclosed herein are capable of facilitating destruction of mRNA containing excessive CUG amplifications.

Thus, tc-DNA-PS AON are described that may be suitably employed for facilitating the destruction of a mutated DM1 mRNA comprising excess CUG amplifications. Such tc-DNA-PS AON comprise 9-27 tricyclo nucleotides, wherein the tc-DNA AON is complementary to a mutated DM1 mRNA comprising one or more 3' CUG amplification(s) and wherein the tc-DNA-PS AON is capable of facilitating the destruction of the DM1 mRNA. Depending upon the precise application contemplated, tc-DNA-PS AON may comprise between 3 and 9; between 4 and 8; or 5, 6, or 7 contiguous repeats of the nucleotide sequence 5'-CAG-3' (SEQ ID NO: 9). An exemplary tc-DNA-PS AON expected to facilitate the destruction of a mutated DM1 comprises the 15-nucleotide sequence 5'-CAGCAGCAGCAGCAG-3' (DM1(CAG5), SEQ ID NO: 10). Another exemplary tc-DNA-PS AON expected to facilitate the destruction of a mutated DM1 comprises the 15-nucleotide sequence:

```
                          (DM1(CAG7), SEQ ID NO: 11)
   5'-CAGCAGCAGCAGCAGCAGCAG-3'.
```

Tricyclo-Phosphorothioate Antisense
Oligonucleotides for the Treatment of Heart
Diseases The most common genetic cause of hypertrophic cardiomyopathy (HCM) are mutations in cardiac myosin-binding protein C (for review see: Schlossarek, S, et al. J Mol Cell Cardiol 50 (2011) 613-620). Very recently, exon skipping has been applied in vitro to modify a mutated cMyBP-C molecule in cMyBP-C ki mouse myocytes (Gedicke, C, Behrens-Gawlik, V, Dreyfus, P A, Eschenhagen, T, Carrier, L. Specific skipping of exons using antisense oligoribonucleotides results in novel molecule in cMyBP-C knock-in mouse myocytes. Circ 201; 122 (Suppl): A 19079). Due to their uptake into cardiac tissue after systemic delivery tc-DNA-PS could be suitably employed to correct mutated cMyBP in cardiac tissue. Of course, the present tc-DNA-PS are also anticipated to be useful for the correction of other proteins in cardiac tissue.

Tricyclo-Phosphorothioate Antisense
Oligonucleotides for the Treatment of CNS
Diseases Unexpectedly, the tc-DNA-PS molecules of the invention have been shown to cross the blood-brain barrier. Accordingly, the present invention relates to a method for providing targeting an oligonucleotide to the CNS, comprising administering to a subject in need thereof a tc-DNA-PS oligonucleotide. In addition, the invention also relates to a method for the treatment of a disease affecting the CNS of a subject in need thereof comprising administering to said subject, in particular a human subject, a tc-DNA-PS molecule of the invention. The tc-DNA-PS is complementary to a target sequence defined such that interaction between the administered tc-DNA-PS and the target sequence provides an effective treatment of said disease. In a particular embodiment, the nucleic acid molecules of the invention can be used for treating diseases that affect both muscles and the CNS. As mentioned above, although Duchenne's muscular dystrophy is mainly characterized by the observed muscular dysfunction, about one third of DMD patients also display cognitive impairment suggesting a noteworthy disruption of neuronal and brain function. The nucleic acid molecules of the invention can thus be used for restoring disrupted neuronal and brain function resulting from abnormal dystrophin.

In addition, the nucleic acid molecules of the invention can be used for treating diseases for which CNS disorders are the main, or one of the main, features. For example, the principles described above for restoring a functional protein (either by exon-skipping or exon inclusion) or for destroying a particular pre-mRNA can be transposed to the treatment of diseases such as spinal muscular amyotrophy, myotonic dystrophy or Huntington's disease.

EXAMPLES

The above disclosure generally describes the present disclosure, which is further exemplified by the following examples. These specific examples are described solely for purposes of illustration, and are not intended to limit the scope of this disclosure. Although specific targets, terms, and values have been employed herein, such targets, terms, and values will likewise be understood as exemplary and non-limiting to the scope of this disclosure.

Duchenne muscular dystrophy (DMD) is an X-linked recessive disorder that affects one in every 3500 live male births (Emery. Neuromuscul. Disord. 1991). It is caused by mutations in the gene that encodes dystrophin, a large protein (427 kDa) found in a variety of tissues, especially in striated muscle fibers and neurons in particular regions of the central nervous system (Kunkel et al., PNAS. 1985; Muntoni F et al., Lancet Neurol. 2003). Dystrophin is located close to the inner surface of the plasma membrane, connecting the actin cytoskeleton to the extracellular matrix through a membrane dystrophin-associated glycoprotein complex (Culligan et al., 1988). Lack of dystrophin makes that muscle fibers are particularly vulnerable to mechanical stress, and undergo recurrent cycles of necrosis. As a result, patients display progressive weakness of skeletal muscles, which are with time replaced by adipofibrotic tissue, leading to loss of ambulation by the age around twelve, whereupon premature death is caused by either respiratory failure or cardiomyopathy between the second and fourth decade. In addition, about one third of DMD patients also display cognitive impairment suggesting a noteworthy disruption of neuronal and brain function (Bresolin et al., Neuromuscul. Disord. 1994).

The full-length dystrophin, translated from a major 14-kb mRNA transcript made of 79 exons, is a modular protein that can fortunately support the deletion of multiple exons provided the open reading frame is preserved (Koenig et al., Cell. 1987). This phenomenon occurs in the clinically milder disease Becker muscular dystrophy (BMD), where deletions that maintain the open reading frame lead to the synthesis of truncated semi-functional forms of dystrophin (Monaco et al. Genomics. 1988). Hence, it was proposed, fifteen years ago, that interfering with the splicing process of elected exons by using antisense oligonucleotides (AON) might be a suitable therapeutic approach for DMD (Matsuo M. Brain Dev. 1996).

Two types of compounds have been extensively tested for antisense-induced exon skipping, the 2'-O-methyl-modified ribose oligomers with a full-length phosphorothioate backbone (2OMe-PS) and the phosphorodiamidate morpholino oligomers (PMO). Both types of antisense molecules have been shown to rescue dystrophin in skeletal muscle after systemic delivery in animal models of DMD and more recently in clinical trials. As things stand, clinical trials using systemic administration of 2'OMe-PS and PMO targeting exon 51 of the dystrophin pre-mRNA were well tolerated with no drug-related serious adverse events (van Deutekom et al., New. Engl. J; Med. 2007; Kinali et al., Lancet Neurol. 2009; Goemans et al., New. Engl. J. Med. 2011; Cirak et al., Lancet 2011). However, these compounds have a major limitation which is that they do not target efficiently the cardiac muscle and do not cross the blood-brain barrier.

Here, we show that systemic delivery of antisense oligomers made of tricyclo-DNA (tc-DNA) nucleotide analogues equally allows dystrophin rescue in skeletal muscles in the mdx mouse model. Moreover, the substitution of sulfur for oxygen in the phosphate ester backbone conferred new properties onto tc-DNA antisenses that were crucial for their biodistribution after systemic administration. Indeed, phosphorothioate (PS)-containing tc-DNA oligomers could now efficiently target the cardiac muscle and, in addition, cross over the blood brain barrier to rescue mutated dystrophin in the heart and the central nervous system.

Material and Methods:
Tricyclo-DNAs.

The synthesis of phosphorothioate tc-DNA followed classical procedures in solid phase oligonucleotide synthesis according to the phosphoramidite approach. The synthesis cycle in which one additional unit is attached to the growing chain consists of four sequential steps (a-d). After chain assembly the oligonucleotide is detached from the solid support and deprotected in the usual way (conc $NH_3$, 55° C., 16 h). Long chain alkylamine controlled pore glass (LCAA-CPG), to which the first tc-nucleoside is bound via a succinyl linker, is used as solid support. Syntheses were generally performed on the 1.3 or 10 µmol scale on a Pharmacia gene assembler plus DNA synthesizer. Tc-PS-oligonucleotides were synthesized with a 5'terminal phosphate or thiophosphate group to ensure chemical stability of the 5'-end. The conditions for each step a)-d) are given below and are optimized for a 10 µmol synthesis.

a) Detritylation: Flush with 3% dichloroacetic acid in 1,2-dichloroethane (DCE) for 1.5 min. Then wash with DCE and $CH_3CN$.

b) Coupling: Phosphoramidite solution (0.1 mM in $CH_3CN$, 400 mL) and activator 5-ethylthiotetrazol (ETT, 0.25M in $CH_3CN$, 600 mL) is applied to the solid support. Coupling time: 9 min. Then wash with $CH_3CN$.

c) Sulfurization: Bis(phenylacetyl)disulfide (PADS) in dry pyridine/$CH_3CN$ 1/1 (0.2M) is flushed over the solid support for 3 min. Then wash with $CH_3CN$ d) Capping: Unreacted 5'-hydroxyl groups are capped using CapA (4-dimethylaminopyridine (DMAP, 0.5M) in $CH_3CN$) and CapB solution (acetic anhydride ($AC_2O$), collidine in $CH_3CN$ (2:3:5)) for 20 s each. Then wash with $CH_3CN$.

The antisense sequence for rescuing the mdx dystrophin pre-mRNA was 15 mer long and targeted the donor slice site of exon 23 (M23D(+2-13)).

```
5'-AACCTCGGCTTACCT-3'        (SEQ ID NO: 1)
```

The other antisense sequences herein described have also been synthesized according to this method.

Animal Experiments

Adult mdx mice (6 to 8 week old) were injected intramuscularly, intravenously or subcutaneously with tc-DNA or tc-DNA-PS as indicated in the results resction under general anesthesia using isofluorane.

DKO mice are generated by crossing (utr+/−, dys−/−) mice, which have been obtained by crossing the utr−/− mice with mdx mice (Deconinck, A. E., Rafael, J. A., Skinner, J. A., Brown, S. C., Potter, A. C., Metzinger, L., Watt, D. J., Dickson, J. G., Tinsley, J. M. and Davies, K. E. (1997) Utrophin-dystrophin-deficient mice as a model for Duchenne muscular dystrophy. Cell, 90, 717-727.) TcDNA were delivered weekly to dKO mice at a dose of 200 mg/kg/wk by intravenous (IV) in the tail vein and subcutaneous (Sc) injections alternatively with mice under general anesthesia. Treated mice were killed at various time points as indicated in the results section by $CO_2$ inhalation. Muscles were snap-frozen in liquid nitrogen-cooled isopentane and stored at −80° C. before further analysis. All dKO experiments were carried out in Biomedical Science Building, University of Oxford, Oxford, UK and performed according to the guidelines and protocols approved by the Home Office.

Muscle Function Analysis

Functional grip strength analysis was performed on treated and control mice at 12 weeks of age using a commercial grip strength monitor (Chatillon, UK). Each mouse was held 2 cm from the base of the tail, allowed to grip a bar attached to the apparatus with their fore paws, and pulled gently until they released their grip. The force exerted was recorded from 4 sequential tests, averaged at 1 min apart.

Specific force and force drop were measured from the extensor digitorum longus (EDL) muscle dissected from the hind leg of the treated and control mice. During dissection and experiments, muscles were bathed in oxygenated (95% $O_2$-5% $CO_2$) Krebs-Hensley solution composing of (mM): NaCl, 118; $NaHCO_3$, 24.8; KCl, 4.75; $KH_2PO_4$, 1.18; $MgSO_4$, 1.18; $CaCl_2$, 2.54; glucose, 10. Contractile properties were measured as previously described (Goyenvalle, A., Babbs, A., Powell, D., Kole, R., Fletcher, S., Wilton, S. D. and Davies, K. E. (2010) Prevention of dystrophic pathology in severely affected dystrophin/utrophin-deficient mice by morpholino-oligomer-mediated exon-skipping. Mol. Ther., 18, 198-205.)

Open Field Activity Monitoring

The Linton AM1053 X, Y, Z IR Activity Monitors were used for open field activity monitoring of the dKO mice. Mice were acclimatised in empty cages for 90 minutes the day prior to actual data collection. The data were collected every 10 minutes over a 90 minute period for 3 consecutive days. The first 3 of the 9 recordings each day were disregarded upon analysis. 22 different activity parameters were measured for each mouse, with total distance travelled, total activity, rearing time and total mobile counts considered the best parameters for monitoring behavioural activity.

Immunohistochemistry and Histology

Sections of 8 μm were cut from at least two-thirds of the muscle length of tibialis anterior, gastrocnemius, quadriceps, gluteus, biceps, triceps, diaphragm, and cardiac muscle at 100 μm intervals. The intervening muscle sections were collected for subsequent RT-PCR analysis. Routine haematoxylin and eosin staining was used to examine overall muscle morphology. The cryosections were then examined for dystrophin expression using the rabbit polyclonal antibody DYS (Novocastra, UK), which was then detected by goat-anti-rabbit IgGs Alexa 488.

RNA Isolation and RT-PCR Analysis

Total RNA was isolated from intervening muscle sections collected during cryosection using TRIzol reagent according to the manufacturer's instructions (Invitrogen, UK). Aliquots of 200 ng of total RNA were used for RT-PCR analysis using the Access RT-PCR System (Promega) in a 50 μl reaction using the external primers Ex 20Fo (5'-CAGAAT-TCTGCCAATTGCTGAG-3'; SEQ ID NO: 12) and Ex 26Ro (5'-TTCTTCAGCTTGTGTCATCC-3'; SEQ ID NO:13). The cDNA synthesis was carried out at 45° C. for 45 min, directly followed by the primary PCR of 30 cycles of 94° C. (30 s), 58° C. (1 min) and 72° C. (2 min). Two microliters of these reactions were then reamplified in nested PCRs by 22 cycles of 94° C. (30 s), 58° C. (1 min) and 72° C. (2 min) using the internal primers Ex 20Fi (5'-CCCA-GTCTACCACCCTATCAGAGC-3'; SEQ ID NO:14) and Ex 26Ri (5'-CCTGCCTTTAAGGCTTCCTT-3'; SEQ ID NO:15). PCR products were analyzed on 2% agarose gels.

Detection of Exon 23-Skipped Dystrophin mRNA in Mdx Central Nervous System

Mdx mice were treated bi-weekly with subcutaneous and intravenous injections of M23D(+2-13) (tc-DNA or tc-DNA-PS backbones) for 8 weeks, with a dose of 100 mg/kg of body weight. A week after the last injection, brains were dissected out and processed for detection of exon 23-skipped dystrophin mRNA. RNA samples were analyzed by nested RT-PCR by using primers (Ex 20Fo (out)/Ex 20Fi (in) annealing exon 20 and Ex 26Ro/Ri122-24 annealing exon 26 and the junction 22-24, respectively) allowing the specific recognition of the skipped messenger as a fragment of 398 bp (Ri22-24 5'-TTATGTGATTCTGTAAATTC-3' SEQ ID NO:16). Note that since the Ri primer anneals specifically the exon 22-exon 24 boundary, the unskipped dystrophin mRNA is not amplified and the 398-bp band can only be detected in samples containing dystrophin mRNAs missing exon 23.

Quantitation of Exon 23 Skipping by Quantitative PCR

RNA was isolated from mouse tissue as described above. Contaminating DNA was removed from the RNA preparations using the Turbo DNA-free system (Ambion). 1 μg aliquots of DNase-treated RNA were then subjected to reverse transcription using the First Strand synthesis system (Invitrogen) with random hexamers according to the manufacturer's instructions. Quantitative PCR was performed using Taqman assays that were designed against the exon 4-5 or exon 22-24 templates using the Custom Assay Design Tool (Applied Biosystems) as described in Goyenvalle et al., Rescue of severely affected dystrophin/utrophin deficient mice through scAAV-U7snRNA-mediated exon skipping; Human Molecular Genetics, 2012, Vol. 21, No. 11 2559-2571. An inventoried 18S assay was utilized as an endogenous control (Applied Biosystems, 4310893E). 50 ng of cDNA was used as input per reaction and all assays were carried out in singleplex. Assays were performed under fast cycling conditions on an Applied Biosystems StepOne Plus thermocycler, and all data were analysed using the comparative Ct method using the associated StepOne analytical software. For a given sample the delta-Ct values of exon 4-5 and exon 22-24 assays were used to calculate a relative abundance of total dystrophin and exon 23-skipped dystrophin mRNA, respectively. Exon 23 skipping was then expressed as a percentage against total dystrophin, as indicated by the exon 4-5 expression level.

Western Blot Analysis

Total protein was extracted from muscle samples with buffer containing 250 mM sucrose, 10 mM Tris-HCl pH 6.7, 20% sodium dodecyl sulfate, 20% glycerol, 10% β-mercaptoethanol, 12.5% of running buffer (Life Technologies) and mix of protease inhibitors (Roche). Samples were denatured at 95° C. for 5 min and centrifuged. Then aliquot was precipitated using the Compat-Able Protein Assay Preparation Reagent Set and quantified with the BCA Protein Assay kit (Pierce) and 50 μg or 100 μg of protein was loaded in a polyacrylamide gel (NuPage 4-12% Bis-Tris, Life Technologies). Gels were electrophoresed for 4-5 hr at 130V and transferred to nitrocellulose membrane overnight at 100 mM. Blots were blocked for 1 hr with 10% non-fat milk in PBS-Tween (PBST) buffer. Dystrophin and α-Actinin proteins were detected by probing the membrane with 1:50 dilution of NCL-DYS1 primary antibody (monoclonal antibody to dystrophin R8 repeat; NovoCastra) and 1:5000 dilution of α-actinin primary antibody (Santa Cruz Biotechnology), respectively, followed by incubation with a mouse horseradish peroxidase-conjugated secondary antibody (1:15000). Western blots were revealed with enhanced chemiluminescence (Thermo Scientific) and ECL Analysis System (ECL-Plus; GE Healthcare). Bands of actin were used to check that the protein load was correct. Membranes were converted to numerical pictures by scanning and band intensities were analyzed using the ImageJ 1.46r software (http://rsb.info.nih.gov/ij/).

Biomarkers Levels Quantification from the Serum

Blood samples were collected from tail bleeds under general anesthesia. Analysis of serum Creatine kinase (CK), alanine aminotransferase (ALT) and aspartate aminotransferase (AST) levels was performed by the pathology laboratory (Mary Lyon Centre, Medical Research Council, Harwell, Oxfordshire, UK).

Statistical Analysis

All results are expressed as mean values±SEM unless otherwise stated. Differences between treated and control cohorts were determined using an unpaired student's t-test.

Figure 1:
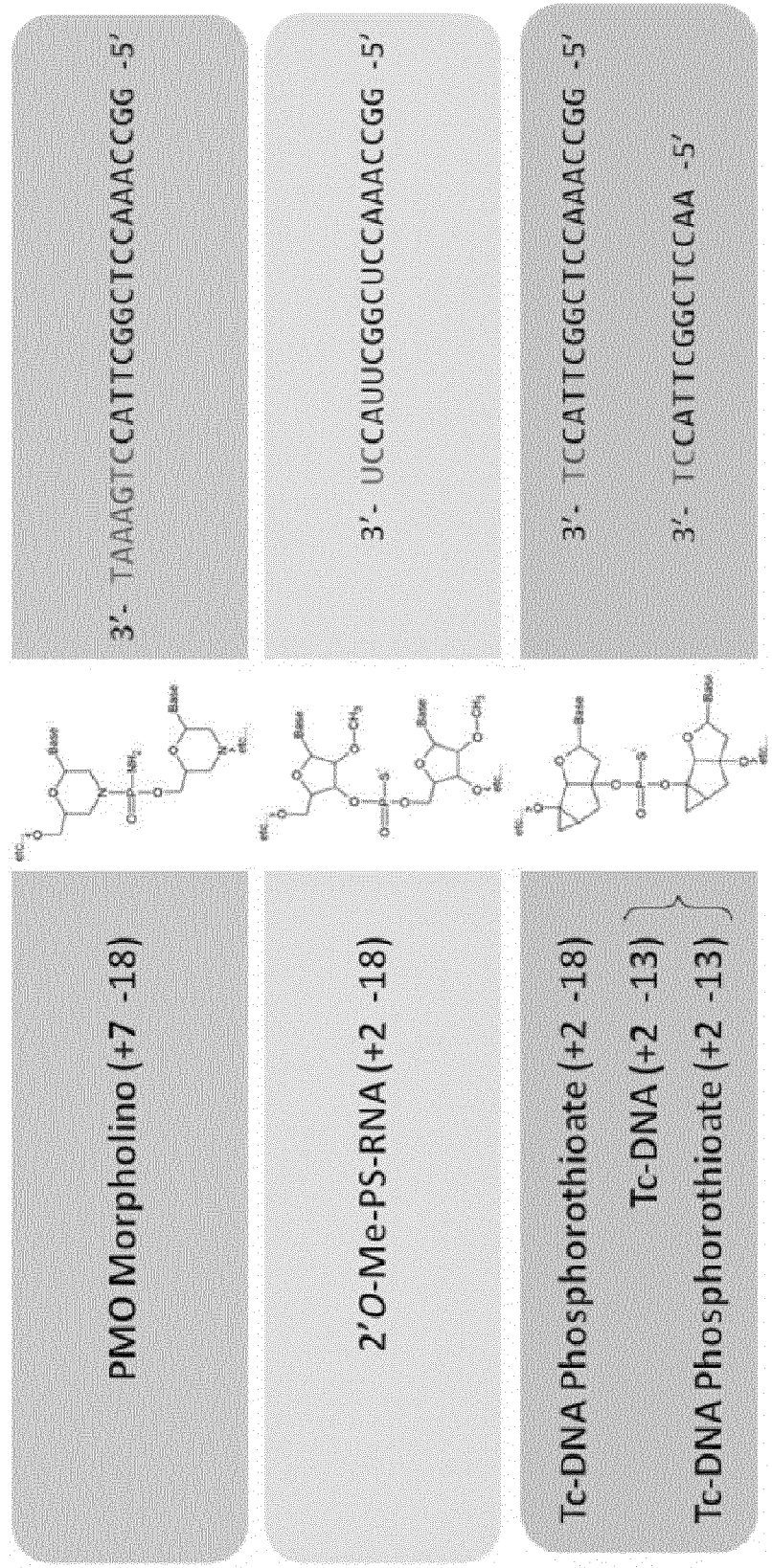
FIG. 1 shows the chemical structures and sequences of PMO morpholino, 2'O-Me-PS-RNA, Tc-DNA and Tc-phosphorothioate DNA oligonucleotides used for exon 23 skipping of dystrophin pre-mRNA in mdx mouse.
Figure 2:
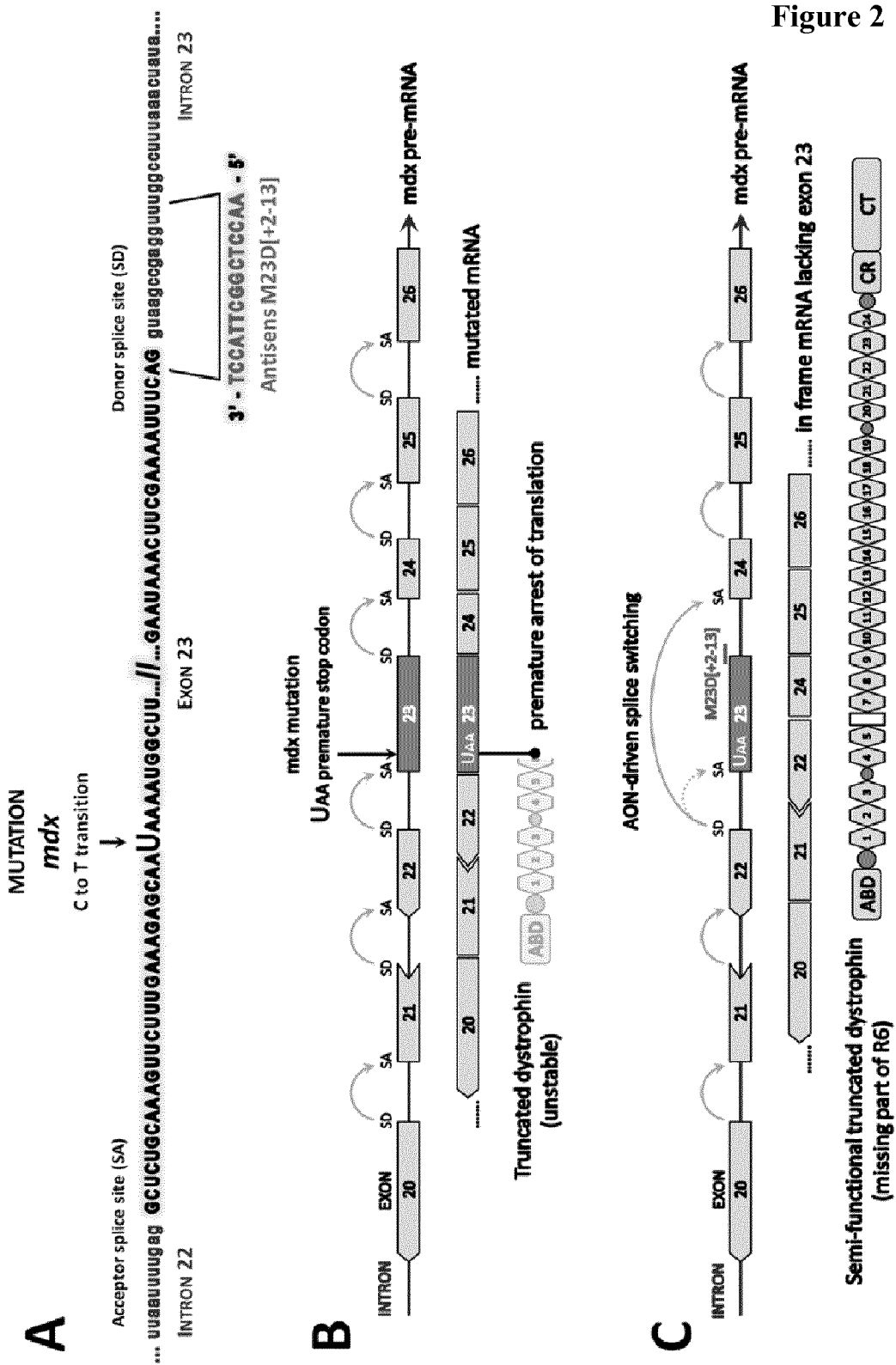
FIG. 2 is a schematic representation of the mdx mutation and splice-switching rationale for dystrophine rescue. The mdx mutation consists in a single base change (C to T transition) in the exon 23 of the dystrophin gene (A). Such a transition generates a premature stop codon (UAA) which abolishes dystrophin synthesis (B). According to the exon phasing around exon 23, it is possible to skip the exon harboring the premature stop codon during the pre-mRNA splicing by using antisense oligonucleotides annealing key motives involved in the definition of exon 23 (C). Resulting mRNA lacking exon 23 can be translated into a truncated but still functional dystrophin.
Figure 3:
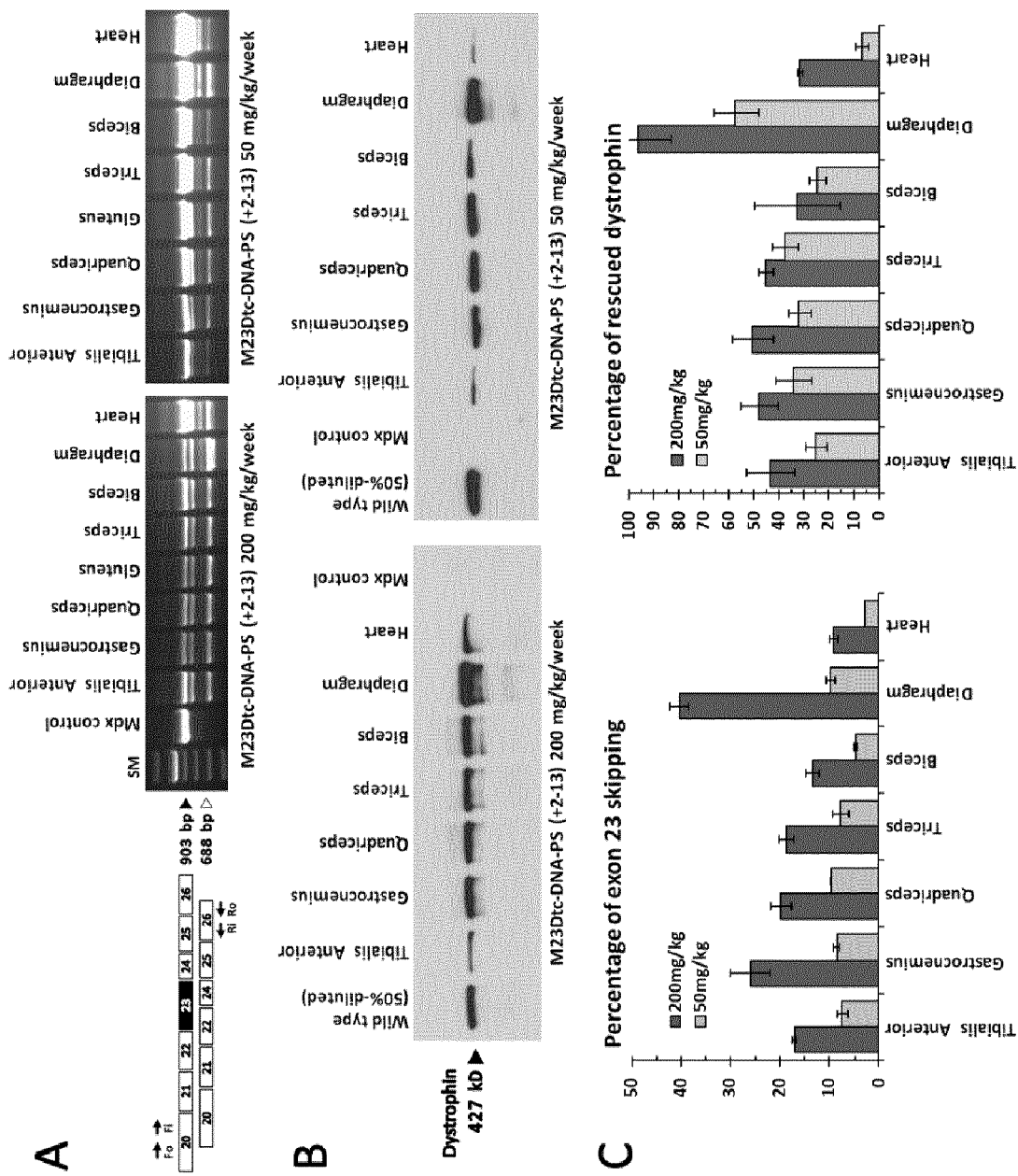
FIG. 3 shows widespread dystrophin rescue in mdx muscles after systemic delivery of tc-DNA-PS (M23D+2-13).
(A) Detection of exon 23-skipped dystrophin mRNA in mdx muscles after systemic delivery of tc-DNA-PS (Dose: 200 or 50 mg/kg of body weight/twice a week; Route: intravenous; Duration: 12 weeks). RNA samples were analyzed at 2 weeks after the end of the treatment by nested RT-PCR as previously described. The 688-bp fragment that corresponds to the exon 23-skipped mRNA was detected in all tested muscles including heart. A diagram is also represented showing the different exons present in the dystrophin pre-mRNA (with or without skipping of exon 23) and the position in exons 20 and 26 of the primers used for nested PCR.
(B) Western blot of total protein (50 µg) extracted from different muscles from treated mice, stained with the NCL-DYS1. Arrows indicate the full-length dystrophin as detected in samples from normal muscle used for comparison. Note that the expected 8 kD difference between wild-type and rescued proteins could not be resolved on this type of gel.
(C) Percentage of exon skipping analyzed by Taqman qPCR (left panel) and percentage of rescued dystrophin assessed by Western blotting (right panel). Exon 23 skipping is expressed as a percentage of total dystrophin, measured by the exon 4-5 expression level, after normalization with an endogenous control. For quantification of levels of dystrophin protein restored in various muscles, membranes were converted to numerical pictures by scanning, and band intensities were analyzed using the ImageJ 1.46r software. Dystrophin levels are expressed as percentage compared with levels in wild type tissue. The analysis involved 3 animals per group.
Figure 4:
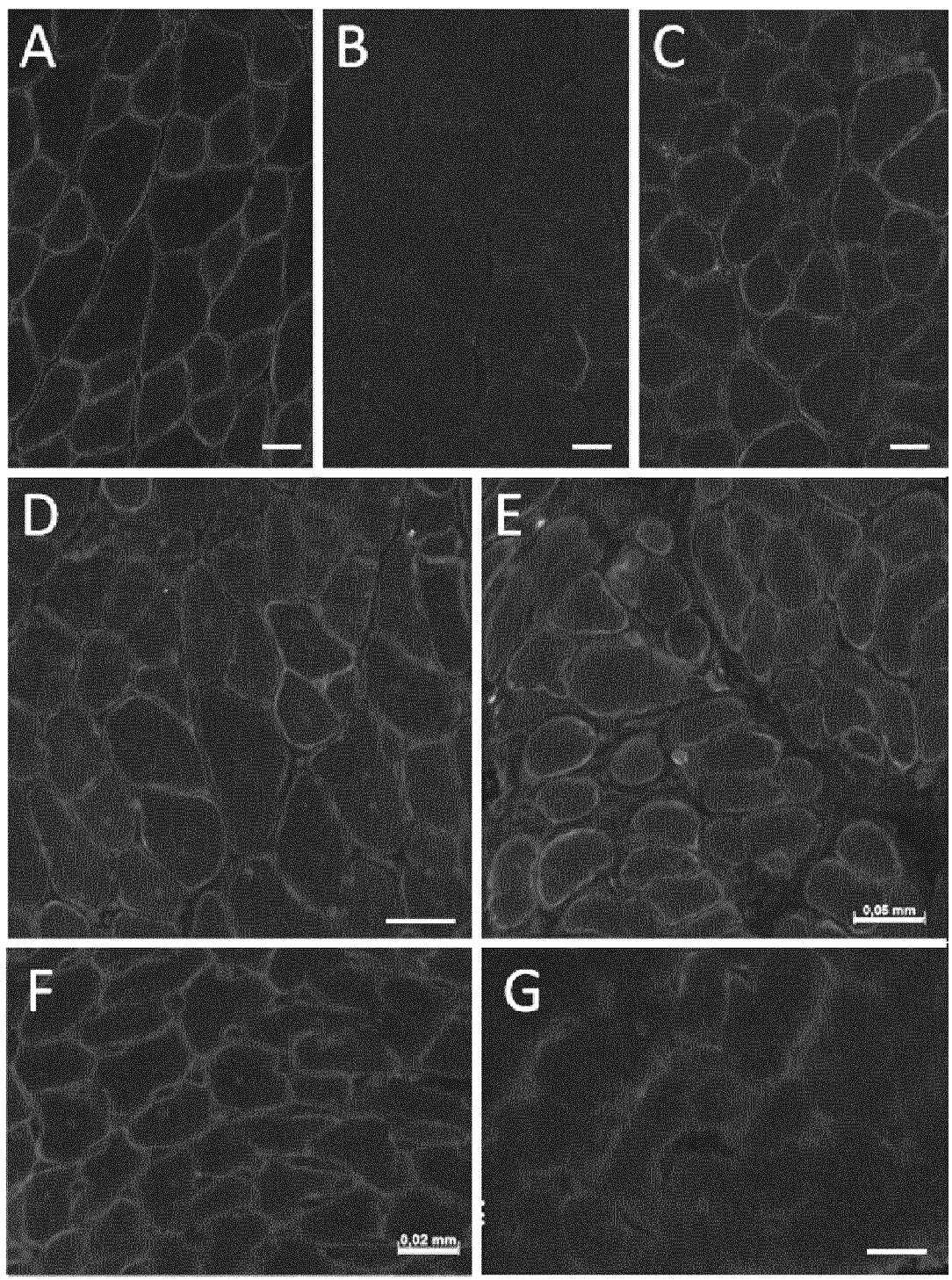
FIG. 4 is a dystrophin immunostaining of normal (A), untreated mdx (B) muscles, and mdx mouse muscles 12 weeks after intravenous injections of tc-PS oligonucleotide (+2-13) (C) gastrocnemius, (D) tibialis anterior, (E) diaphragm. (F and G) show dystrophin staining in heart from wild type and treated mdx, respectively. Nuclei were counterstained with Dapi.
Legend: Detection of dystrophin in mdx muscles after systemic treatment with the tc-DNA-PS oligomer M23D(+2-13). Mdx mice were treated weekly with intravenous injections of M23D(+2-13) for 12 weeks, with a dose of 200 mg/kg of body weight. Two weeks after the last injection, muscles were dissected and processed for immuno fluorescence analysis involving staining with the NCL-DYS2 monoclonal dystrophin antibody. (A and B) show transverse sections of normal and mdx muscles. (C, D and E) show dystrophin immuno-labeling of muscle samples from treated mdx: gastrocnemius, tibialis anterior and diaphragm, respectively. (F and G) show dystrophin staining in normal heart and treated mdx, respectively.
Figure 5:
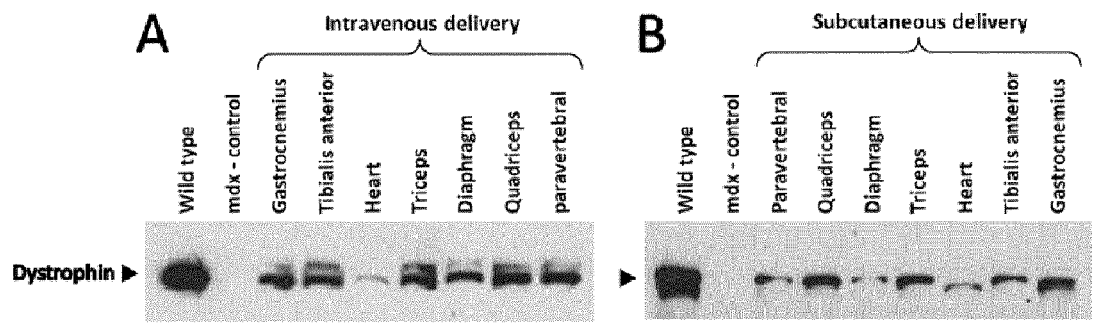
FIG. 5 presents experiment on the comparison of intravenous versus subcutaneous delivery of tc-PS oligonucleotide.
Mdx animals were treated for 8 weeks with tc-DNA-PS (M23D+2-13) 100 mg/kg twice a week delivered either by intravenous (A) or subcutaneous (B) injections. Both routes of administration give rise to similar out comes as shown by Western blot analysis (each lane was loaded with 100 µg of total protein) from muscle samples stained with the NCL-DYS1 monoclonal antibody. Analysis was done 2 weeks after the end of the treatment. Arrows indicate the full-length dystrophin as detected in the lane loaded with wild type muscle.
Figure 6:
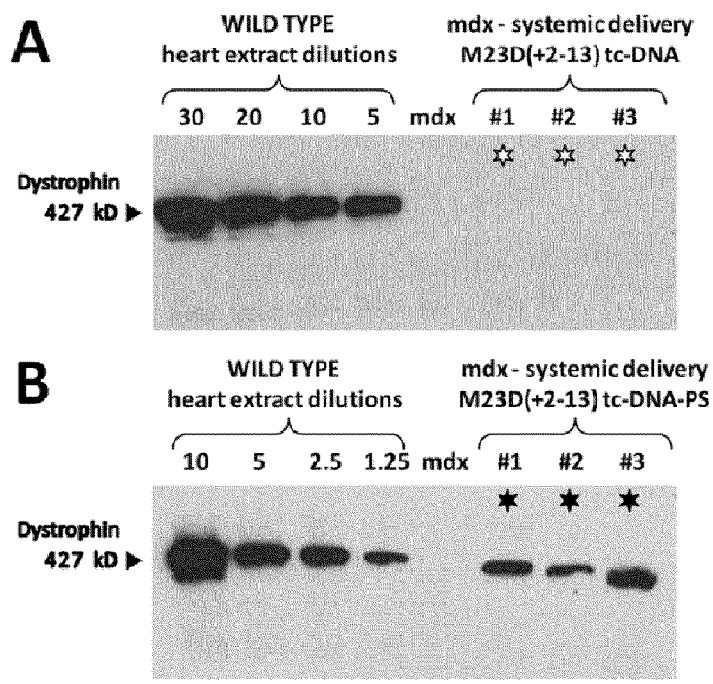
FIG. 6 presents photographs of western blots showing dystrophin protein expression in cardiac muscle in mdx mice after systemic treatment with tc-DNA-PS oligomer M23D(+2-13).
Results of Western blot analysis (using the dystrophin NCL-DYS1 monoclonal antibody) of total protein extracts (100 µg loaded) isolated from the hearts of 3 mdx mice treated with the M23D(+2-13) tc-DNA oligomer (white stars) (bi-weekly injections—subcutaneous and intravenous—at 100 mg/kg for 8 weeks) (A); and 3 mdx mice treated in the same conditions with the M23D(+2-13) tc-DNA-phosphorothioate (—PS) oligomer (black stars) (B). The arrow indicates the full-length 427 kD dystrophin, as detected in lanes of corresponding wild type controls for semi-quantitative comparison of dystrophin signal detection. Wild type heart extract were diluted 30 to 5% for (A) and 10 to 1.25% for (B) in mdx heart extracts in order to normalize the loading amount of protein to 100 µg per lane.
Figure 7:
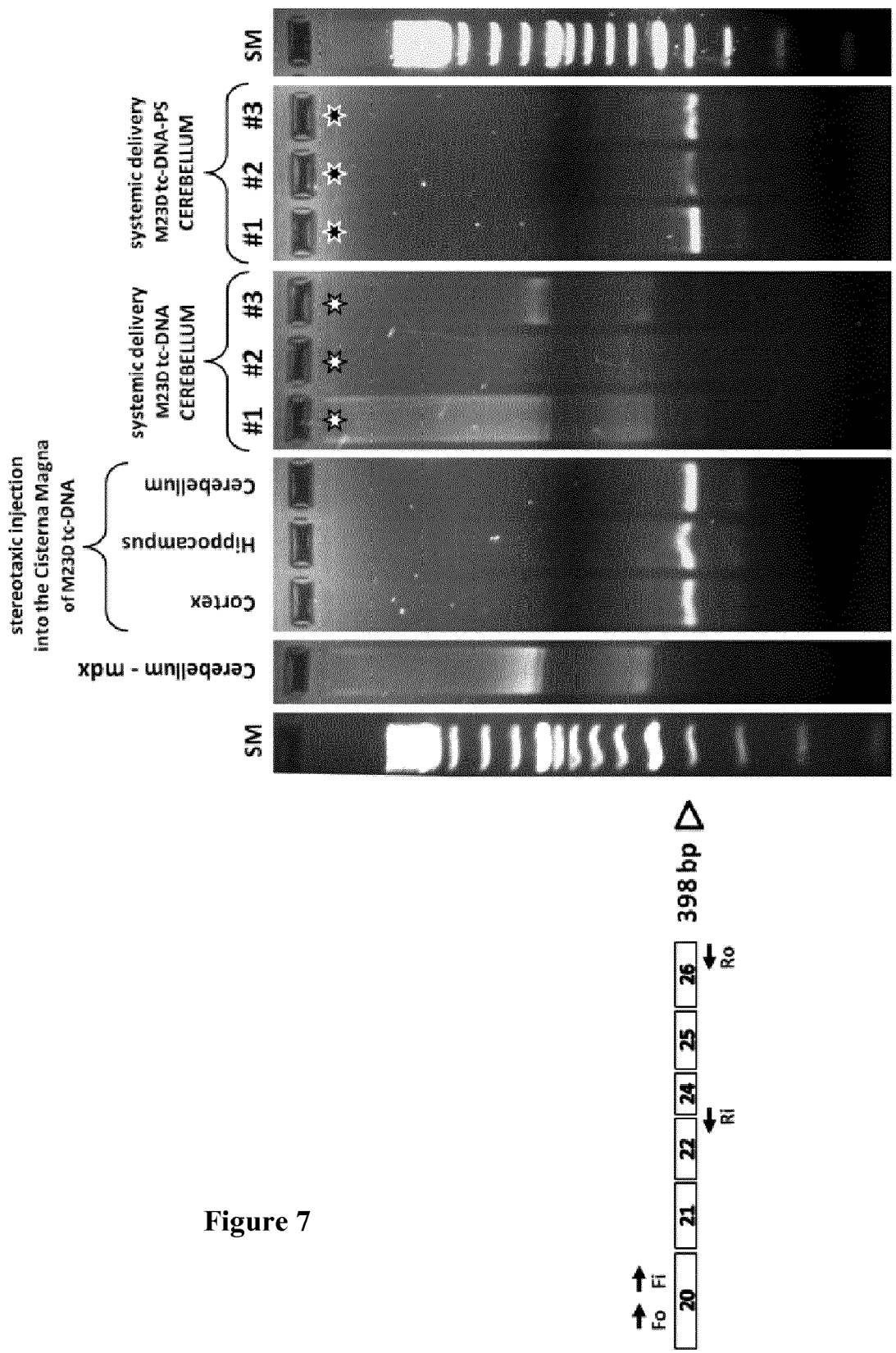
FIG. 7 is an agarose gel of nested PCR reactions showing skipping of dystrophin pre-mRNA in the CNS of mdx mice treated with either the tc-DNA M23D (+2-13) oligonucleotide or the tc-DNA-PS M23D (+2-13) oligonucleotide. Injections have been carried out either systemically or via stereotaxic injection into the Cisterna Magna.
Legend: Detection of exon 23-skipped dystrophin mRNA in mdx central nervous system after systemic treatment with either tc-DNA or tc-DNA-PS M23D(+2-13) oligomers. Mdx mice were treated bi-weekly with subcutaneous and intravenous injections of M23D(+2-13) (tc-DNA or tc-DNA-PS backbones) for 8 weeks, with a dose of 100 mg/kg of body weight. A week after the last injection, brains were dissected out and processed for detection of exon 23-skipped dystrophin mRNA. RNA samples were analyzed by nested RT-PCR by using primers (Fo (out)/Fi (in) annealing exon 20 and Ro/Ri annealing exon 26 and the junction 22-24, respectively) allowing the specific recognition of the skipped messenger as a fragment of 398 bp. Note that since the Ri primer anneals specifically the exon 22-exon 24 boundary, the unskipped dystrophin mRNA is not amplified and the 398-bp band can only be detected in samples containing dystrophin mRNAs missing exon 23. SM, size markers; lane 2—untreated mdx cerebellum; lanes 3 to 5—cortex, hippocampus and cerebellum in mdx CNS one month after a stereotaxic injection of 400 µg of M23D(+2-13) tc-DNA in the Cisterna Magna; lanes 6 to 8—cerebellum in 3 mdx mice after systemic treatment with M23D(+2-13) tc-DNA (white*); lanes 9 to 11—cerebellum in 3 mdx mice after systemic treatment with M23D(+2-13) tc-DNA phosphorothioate (—PS) (black*). Detection of exon 23 skipping in cortex, hippocampus and cerebellum after 5 weeks of systemic treatment using a dose of only 25 mg/kg/week of M23D(+2-13) tc-DNA-PS. Note that systemic treatment with the tc-DNA-PS oligomer M23D(+2-13) rescues the dystrophin mRNA in CNS following systemic administration, while the tc-DNA form requires intra-cerebral delivery.
Figure 8:
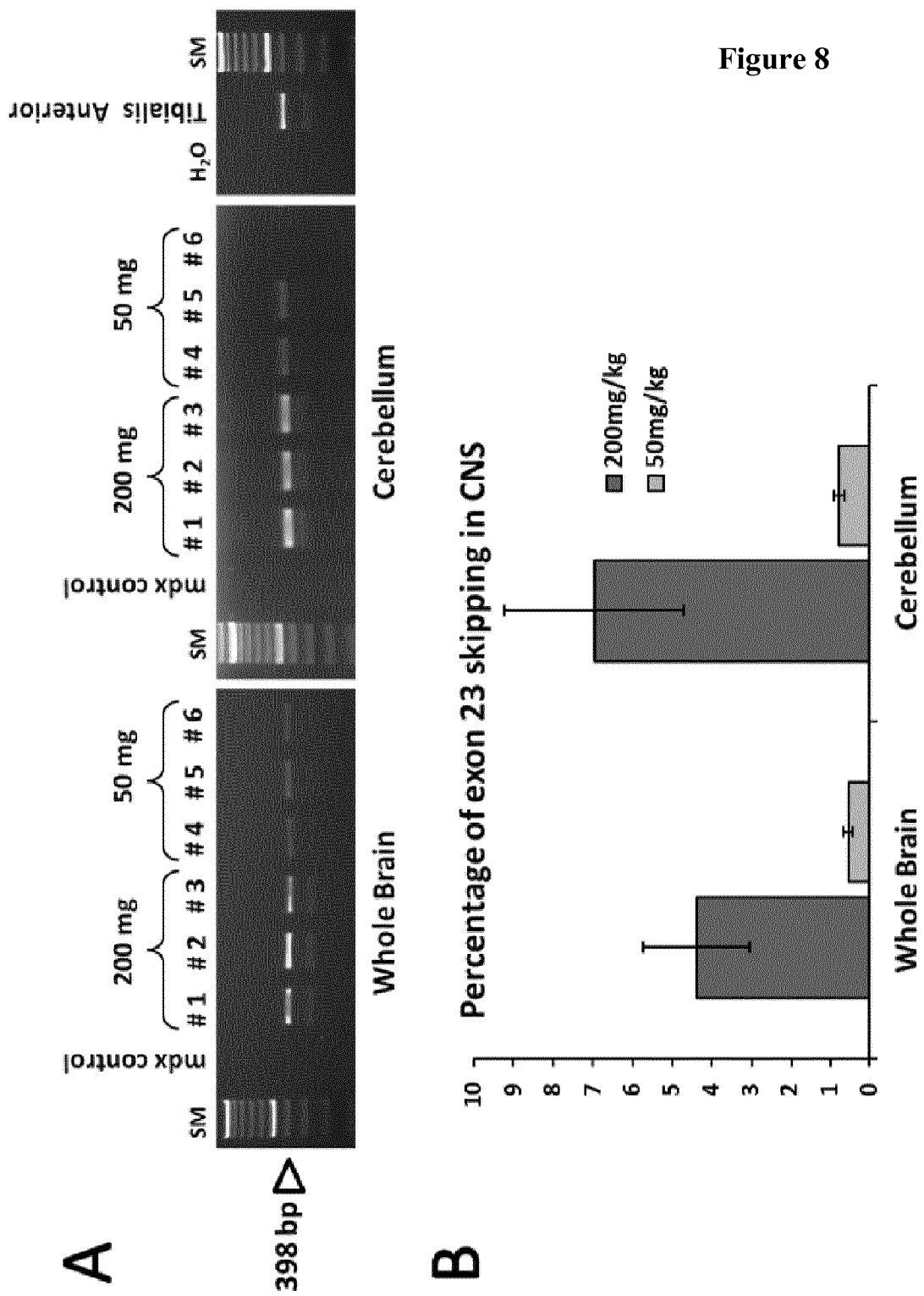
FIG. 8 presents dystrophin mRNA rescue in the CNS of mdx mice following systemic delivery of tc-DNA-PS (M23D+2-13) at two different dosages.

Example 1—In Vivo Evaluation of Tc-DNA-PS Antisense Oligonucleotides for the Treatment of a Dystrophin-Mediated Muscular Dystrophy Adult mdx mice were treated systemically for 12 weeks by using subcutaneous and/or intravenous injections of tc-DNA-PS M23D (+2-13) oligomer at either 200 or 50 mg/kg of body weight per week. Two weeks after the last injection, muscles were harvested and RNA samples were analyzed by nested RT-PCR with primers in exons 20 and 26 of the dystrophin gene. FIG. 3A shows the detection of exon 23-skipped dystrophin mRNA in a number of skeletal muscles from treated animals. The 903-bp band corresponds to the unskipped dystrophin mRNA enclosing the mdx non-sense mutation, while the shorter 688-bp fragment corresponds to the exon 23-skipped mRNA. It is remarkable that systemic treatment with the phosphorothioate-containing oligomer induces significant rescue of the dystrophin mRNA in various skeletal muscles (i.e. tibialis anterior, gastrocnemius, quadriceps, gluteus, triceps, biceps, diaphragm), including respiratory muscles, as well as in cardiac muscle. Consistent with the generation of skipped transcripts, the dystrophin protein was readily detected both by Western blot analysis (FIG. 3B) and by immunofluorescence on tissue sections (FIG. 4). The levels of dystrophin mirrored those of the rescued mRNA and the skipping procedure generated immunoreactive protein species with a mobility around 427 kDa. The expected 8 kD difference between wild type and rescued proteins could not be resolved on the type of gel used in this study. Importantly, both modes of delivery, intravenous and subcutaneous, gave rise to similar widespread dystrophin rescue in mdx as shown in FIG. 5. Whatever the mode of systemic delivery, oligonucleotides made using the normal tc-DNA backbone (i.e. with normal phosphodiester internucleoside bonding) were unable to significantly target the cardiac muscle. This was only achieved with the phosphorothioate (—PS) backbone as illustrated in FIG. 6. The phosphorothioate modification conferring substantial pharmacokinetic benefit, we investigated whether such adaptation could allow the oligonucleotides cross the blood brain barrier. Indeed, oligonucleotides using the normal tc-DNA backbone were shown to rescue the dystrophin mRNA when delivered into the cerebrospinal fluid after stereotaxic injection into the cistern magna, suggesting that they could cross the ependimal epithelium. However, such compounds were inefficient when delivered intravenously and/or subcutaneously demonstrating that they could not cross the blood-brain barrier (FIG. 7). In fact, this was only successfully achieved when using the phosphorothioated (—PS) forms of tc-DNAs (FIG. 8), thus demonstrating their ability to access all main tissues where dystrophin had to be ideally restored: skeletal muscles, heart and CNS.

Therapeutic effect of systemic delivery of tc-DNA-PS (M23D+2-13) was confirmed by the significant decrease of creatine kinase levels in the serum of treated animals, indicating that the amount of rescued dystrophin was appropriate to protect fibers from exercise-induced damage without obvious toxicity as accounted by the levels of ALT and AST in blood, which did not increase at whatever concentration of oligomers (FIGS. 9A and B). Muscle improvement was also assessed by testing the specific force of treated muscles which was significantly enhanced (FIG. 9C). More importantly, the percentage of force drop, a characteristic feature of dystrophic muscle assessed by measuring the force deficit following a series of eccentric contractions, was reduced in treated animals, confirming that muscle fibers in treated animals were much more resistant (FIG. 9D).

Clinical relevance was appraised in the dKO transgenic mouse, a more severe DMD model, which lacks both dystrophin and utrophin, leading to progressive muscle wasting, impaired mobility and premature death. As for mdx, systemic treatment of dKO with tc-DNA-PS allowed significant rescue of dystrophin in all tissue compartments (FIG. 10). Percentage of exon skipping was assessed by quantitative RT-PCR at different time points after the beginning of the treatment showing that there was a cumulative effect over the duration of the treatment. mRNA rescue was almost complete in the diaphragm after 20 weeks and one could expect that the other skeletal muscles would reach that level of skipping within 40 weeks and later for heart and brain for which the uptake of the oligomer seems lower (FIG. 11). Nonetheless, levels of dystrophin rescue in dKO after 12 weeks of treatments provide significant clinical benefit. Treated mice did not show the characteristic kiphosis, CK levels were decreased while mice were more physically active and displayed improved physiological parameters (FIG. 12). Although the pharmacokinetic studies showed that the oligonucleotides disappeared from serum within minutes after the intravenous injection (FIG. 13A), it appears that they have a long lasting effect once inside the target tissue. This is suggested by the fact that skipping levels were found of about half of their maximal value 13 weeks after the end of the treatment (FIG. 13B). This long lasting effect is confirmed in the results presented in FIG. 14. It is likely that tc-DNA-PS are stable in cells and could be re-employed over time thus limiting the need to fill up tissues as often it would be required if these oligonucleotides were destroyed or tittered by their mRNA targets.

Example 2—Effect of the Delivery of a Tc-DNA-PS (ISS7) Targeting Exon 7 of SMN2

The SMA mouse model (FVB.Cg-Tg(SMN2)2Hung Smn1tm1Hung/J) was used. SMA Type III mice (FVB.Cg-Tg(SMN2)2Hung Smn1$^{tm1Hung}$/J) are knock out for Smn (Smn1−/−) and contain a SMN2 transgene made of two tandem copies of the human SMN2 gene. These animals display typical features including necrosis of the tail starting at about one month of age. Such a necrosis progressively extends to the pinnae of the ears and feet and late in life these animals present with muscle weakness. The photograph in FIG. 15 shows 3 type III individuals (one month old). The upper one is the untreated control; the two others were treated with tc-DNA-PS (ISS7): they received a single injection ICV (intracerebroventricular) at birth (5 µl containing 20 µg of tc-DNA-PS (ISS7)) and repeated SC (subcutaneous) injections once a week at a dose of 200 mg/kg.

We conclude that tc-DNA-PS oligomers represent a possible drug candidate for SMA therapy. Furthermore, since this type of oligonucleotide can spontaneously cross the blood brain barrier (see mdx section), it is likely that tc-DNA-PS would not necessarily required intracerebral administration to efficiently redirect SMN2 splicing in CNS.

Example 3—Evaluation of Tc-DNA and Tc-DNA-PS for DM1

DM1 myoblasts with 800 CTG repeats were transfected with increasing concentration of tc-DNA-CAG7 (SEQ ID NO: 11). After 3 days in culture, expression of both normal and mutant CUGexp-DMPK (dystrophia myotonica-protein kinase) mRNAs was analyzed by Northern blot. The ratio of mutant CUGexp-DMPK vs. normal DMPK mRNAs was quantified. A dose dependent decrease of the mutant CUGexp-DMPK mRNA without hanging of the normal DMPK mRNA showed that the treatment with the oligonucleotide results in the specific destruction of mutant CUGexp-DMPK (see FIG. 16)

In another experiment, DM1 myoblasts with expanded CTG (>800 CTG) were transfected with 10 µg of tc-DNA-PS-CAG7. After 3 days in culture, expression of normal and mutant CUGexp-DMPK mRNAs was analyzed by Northern blot. The ratio of mutant CUGexp-DMPK vs. normal DMPK mRNAs was quantified (FIG. 17 upper lane). The nuclear aggregates of CUG expanded RNAs (foci) were detected by FISH and the number of cells without CUGexp-RNA nuclear aggregates was quantified (FIG. 17 lower lane). The results show that DM1 myoblasts transfected with the oligonucleotide have i) decreased level of mutant CUGexp-DMPK mRNAs without any change of the normal DMPK mRNAs; ii) increased number of cells without nuclear aggregates The effect of the tc-DNA-PS-CAG7 oligonucleotide was then assessed in vivo. Since the oligonucleotide targets the CUG expanded RNA of the DMPK transcripts without affecting the normal DMPK transcripts in DM1 muscle cells, we decided to evaluate the effect of the oligonucleotide in a DM1 mouse model expressing CUG expanded RNA in the 3' non coding region of human skeletal actin (HSA) gene. This DM1 mouse model has already been used to evaluate both CAG8 morpholino and CAG8 2'-O-Me ASO because it showed alternative splicing misregulation of several RNA transcripts as well as myotonia, which results from misssplicing of C1C-1 pre-mRNAs.

Tibialis anterior TA muscles of HSA-LR mice expressing 250CTG in the 3'UTR of human skeletal actin (HSA) gene were injected with increasing concentration of tc-DNA-PS-CAG7. Controlateral TA muscles were injected with saline and used as control. After 2 weeks, expression of HSA and MSA (mouse skeletal actin) mRNAs was analyzed by Northern blot. The ratio of HSA vs. MSA mRNAs was quantified. FIG. 18 shows that intramuscular injection of the oligonucleotide results in a marked decrease of CUGexp-RNAs.

TA muscles of HSA-LR mice expressing 250CTG in the 3'UTR of the human skeletal actin (HSA) gene were also injected with 30 µg of tc-DNA-PS-CAG7. Controlateral TA muscles were injected with saline and used as control. After 1 and 2 weeks, expression of HSA and MSA (mouse skeletal actin) mRNAs was analyzed by Northern blot. The ratio of HSA vs. MSA mRNAs was quantified. FIG. 19 shows that decreased level of CUGexp-RNAs following intramuscular injection of the oligonucleotide was already observed after 1 week.

At last, Gastrocnemius GA muscles of HSA-LR mice expressing 250CTG in the 3'UTR of human skeletal actin (HSA) gene were injected with 90 µg of tc-DNA-PS-CAG7. Controlateral GA muscles were injected with saline and used as control. Expression of HSA and MSA (mouse skeletal actin) mRNAs was analyzed by Northern blot after 2, 4 and 8 weeks. The ratio of HSA vs. MSA mRNAs was quantified. FIG. 20 shows that intramuscular administration of the oligonucleotide causes an efficient destruction of CUGexp-RNAs and the effect is sustained between 4 to 8 months after treatment.

The invention claimed is:

1. A nucleic acid molecule comprising tricyclo-nucleosides joined by internucleoside phosphorothioate linkages (3'-OPS—O-5' linkages).

2. The nucleic acid molecule according to claim 1, comprising between 3 and 50 nucleotides.

3. The nucleic acid molecule according to claim 1, which is complementary to a target sequence.

4. The nucleic acid molecule according to claim 3, the nucleic acid molecule being an antisense oligonucleotide complementary to a portion of a RNA encoded by a gene.

5. The nucleic acid molecule of claim 1, comprising or consisting of the sequence selected in the group consisting of SEQ ID NOs: 1 to 11.

6. A pharmaceutical composition comprising a nucleic acid molecule according to claim 1, in a pharmaceutically acceptable carrier.

7. The pharmaceutical composition according to claim 6, said composition being an injectable composition, in particular a composition for intravenous injection.

8. A pharmaceutical composition comprising tricyclo-nucleosides joined by internucleoside phosphorothioate linkages (3'-OPS—O-5' linkages), comprising between 15 and 50 nucleotides and a pharmaceutically acceptable carrier, the composition being adapted for intravenous injection.

* * * * *

SEQUENCE LISTING

```
<160> NUMBER OF SEQ ID NOS: 16

<210> SEQ ID NO 1
<211> LENGTH: 15
<212> TYPE: DNA
<213> ORGANISM: Artificial
<220> FEATURE:
<223> OTHER INFORMATION: tc-DNA PS AON M23D (+02-13)
<220> FEATURE:
<221> NAME/KEY: misc_feature
<223> OTHER INFORMATION: tricyclo-phosphorothiate DNA

<400> SEQUENCE: 1
aacctcggct tacct                                                    15

<210> SEQ ID NO 2
<211> LENGTH: 20
<212> TYPE: DNA
<213> ORGANISM: Artificial
<220> FEATURE:
<223> OTHER INFORMATION: tc-DNA PS AON M23D (+2-18)
<220> FEATURE:
<221> NAME/KEY: misc_feature
<223> OTHER INFORMATION: tricyclo-phosphorothiate DNA

<400> SEQUENCE: 2
ggccaaacct cggcttacct                                               20

<210> SEQ ID NO 3
<211> LENGTH: 15
<212> TYPE: DNA
<213> ORGANISM: Artificial
```

```
<220> FEATURE:
<223> OTHER INFORMATION: tc-DNA PS AON H51 (+68+82)
<220> FEATURE:
<221> NAME/KEY: misc_feature
<223> OTHER INFORMATION: tricyclo-phosphorothiate DNA

<400> SEQUENCE: 3
agaaatgcca tcttc                                                    15

<210> SEQ ID NO 4
<211> LENGTH: 15
<212> TYPE: DNA
<213> ORGANISM: Artificial
<220> FEATURE:
<223> OTHER INFORMATION: tc-DNA PS AON H51 (+70+84)
<220> FEATURE:
<221> NAME/KEY: misc_feature
<223> OTHER INFORMATION: tricyclo-phosphorothiate DNA

<400> SEQUENCE: 4
aaatgccatc ttcct                                                    15

<210> SEQ ID NO 5
<211> LENGTH: 15
<212> TYPE: DNA
<213> ORGANISM: Artificial
<220> FEATURE:
<223> OTHER INFORMATION: tc-DNA PS AON H51 (+73+87)
<220> FEATURE:
<221> NAME/KEY: misc_feature
<223> OTHER INFORMATION: tricyclo-phosphorothiate DNA

<400> SEQUENCE: 5
tgccatcttc cttga                                                    15

<210> SEQ ID NO 6
<211> LENGTH: 16
<212> TYPE: DNA
<213> ORGANISM: Artificial
<220> FEATURE:
<223> OTHER INFORMATION: tc-DNA PS AON H51(+40+55)
<220> FEATURE:
<221> NAME/KEY: misc_feature
<223> OTHER INFORMATION: tricyclo-phosphorothiate DNA

<400> SEQUENCE: 6
gcagtttcct tagtaa                                                   16

<210> SEQ ID NO 7
<211> LENGTH: 15
<212> TYPE: DNA
<213> ORGANISM: Artificial
<220> FEATURE:
<223> OTHER INFORMATION: tc-DNA PS AON SMN2i7(10;25)
<220> FEATURE:
<221> NAME/KEY: misc_feature
<223> OTHER INFORMATION: tricyclo-phosphorothiate DNA

<400> SEQUENCE: 7
ctttcataat gctgg                                                    15

<210> SEQ ID NO 8
<211> LENGTH: 13
<212> TYPE: DNA
<213> ORGANISM: Artificial
<220> FEATURE:
<223> OTHER INFORMATION: tc-DNA PS AON SMN2e7(39;51)
<220> FEATURE:
<221> NAME/KEY: misc_feature
```

<223> OTHER INFORMATION: tricyclo-phosphorothiate DNA

<400> SEQUENCE: 8
ttaatttaag gaa                                                    13

<210> SEQ ID NO 9
<211> LENGTH: 3
<212> TYPE: DNA
<213> ORGANISM: Artificial
<220> FEATURE:
<223> OTHER INFORMATION: DNA repeat

<400> SEQUENCE: 9 cag                                                                3

<210> SEQ ID NO 10
<211> LENGTH: 15
<212> TYPE: DNA
<213> ORGANISM: Artificial
<220> FEATURE:
<223> OTHER INFORMATION: tc-DNA PS AON DM1(CAG5)
<220> FEATURE:
<221> NAME/KEY: misc_feature
<223> OTHER INFORMATION: tricyclo-phosphorothiate DNA

<400> SEQUENCE: 10
cagcagcagc agcag                                                  15

<210> SEQ ID NO 11
<211> LENGTH: 21
<212> TYPE: DNA
<213> ORGANISM: Artificial
<220> FEATURE:
<223> OTHER INFORMATION: tc-DNA PS AON DM1(CAG7)
<220> FEATURE:
<221> NAME/KEY: misc_feature
<223> OTHER INFORMATION: tricyclo-phosphorothiate DNA

<400> SEQUENCE: 11
cagcagcagc agcagcagca g                                           21

<210> SEQ ID NO 12
<211> LENGTH: 22
<212> TYPE: DNA
<213> ORGANISM: Artificial
<220> FEATURE:
<223> OTHER INFORMATION: Exon 20 Fo primer

<400> SEQUENCE: 12
cagaattctg ccaattgctg ag                                          22

<210> SEQ ID NO 13
<211> LENGTH: 20
<212> TYPE: DNA
<213> ORGANISM: Artificial
<220> FEATURE:
<223> OTHER INFORMATION: Exon 26 Ro primer

<400> SEQUENCE: 13
ttcttcagct tgtgtcatcc                                             20

<210> SEQ ID NO 14
<211> LENGTH: 24
<212> TYPE: DNA
<213> ORGANISM: Artificial
<220> FEATURE:
<223> OTHER INFORMATION: Exon 20 Fi primer

```
<400> SEQUENCE: 14
cccagtctac caccctatca gagc                                          24

<210> SEQ ID NO 15
<211> LENGTH: 20
<212> TYPE: DNA
<213> ORGANISM: Artificial
<220> FEATURE:
<223> OTHER INFORMATION: Exon 26 Ri primer

<400> SEQUENCE: 15
cctgccttta aggcttcctt                                               20

<210> SEQ ID NO 16
<211> LENGTH: 20
<212> TYPE: DNA
<213> ORGANISM: Artificial
<220> FEATURE:
<223> OTHER INFORMATION: Ri22-24 primer

<400> SEQUENCE: 16
ttatgtgatt ctgtaaattc                                               20
```